United States Patent
Caballero

(10) Patent No.: US 7,393,598 B2
(45) Date of Patent: Jul. 1, 2008

(54) LIGHT EMITTING MOLECULES AND ORGANIC LIGHT EMITTING DEVICES INCLUDING LIGHT EMITTING MOLECULES

(75) Inventor: Gabriel Joseph Caballero, Longmont, CO (US)

(73) Assignee: HCF Partners, L.P., Houston, TX (US)

( * ) Notice: Subject to any disclaimer, the term of this patent is extended or adjusted under 35 U.S.C. 154(b) by 330 days.

(21) Appl. No.: 10/798,224

(22) Filed: Mar. 10, 2004

(65) Prior Publication Data

US 2005/0202273 A1    Sep. 15, 2005

(51) Int. Cl.
*H01J 1/62* (2006.01)
*H01L 29/08* (2006.01)

(52) U.S. Cl. .................. 428/690; 428/917; 313/503; 257/40; 257/88

(58) Field of Classification Search .................. 428/690, 428/917; 313/504, 506, 503, 509, 512; 257/40
See application file for complete search history.

(56) References Cited

U.S. PATENT DOCUMENTS

| | | | |
|---|---|---|---|
| 4,197,142 A | 4/1980 | Bolton et al. |
| 4,775,820 A | 10/1988 | Eguchi et al. |
| 5,010,451 A | 4/1991 | Ueyama et al. |
| 5,057,878 A | 10/1991 | Geddes et al. |
| 5,294,870 A | 3/1994 | Tang et al. |
| 5,525,811 A | 6/1996 | Sakurai et al. |
| 5,677,545 A | 10/1997 | Shi et al. |
| 5,747,345 A | 5/1998 | Weber, II et al. |
| 5,811,833 A | 9/1998 | Thompson |
| 5,840,897 A | 11/1998 | Kirlin et al. |
| 5,946,550 A | 8/1999 | Papadimitrakopoulos |
| 6,028,265 A | 2/2000 | Ono et al. |
| 6,030,700 A | 2/2000 | Forrest et al. |
| 6,045,930 A | 4/2000 | Thompson et al. |
| 6,048,630 A | 4/2000 | Burrows et al. |
| 6,060,327 A | 5/2000 | Keen |
| 6,096,273 A | 8/2000 | Kayyem et al. |
| 6,114,099 A | 9/2000 | Liu et al. |
| 6,146,767 A | 11/2000 | Schwartz |
| 6,169,291 B1 | 1/2001 | Metzger et al. |
| 6,231,983 B1 | 5/2001 | Lee et al. |

(Continued)

OTHER PUBLICATIONS

J. C. Aguilar et al., Design, synthesis and evaluation of diazadibenzocrown ethers as $Pb^{2+}$ extractants and carriers in plasticized cellulose triacetate membranes, Talanta 54:1195-1204, 2001.

(Continued)

*Primary Examiner*—Terrel Morris
*Assistant Examiner*—Camie S Thompson
(74) *Attorney, Agent, or Firm*—Greenlee, Winner and Sullivan, P.C.

(57) ABSTRACT

Light emitting molecules and organic light emitting devices comprising such light emitting molecules are described. In one embodiment, a light emitting molecule comprises an anchoring group and a charge transport group having a first end and a second end. The first end of the charge transport group is bonded to the anchoring group. The charge transport group is configured to provide transport of electrical energy, and the transport of electrical energy is substantially one-dimensional. The light emitting molecule also comprises a light emissive group bonded to the second end of the charge transport group and a charge transfer group bonded to the light emissive group.

39 Claims, 13 Drawing Sheets

U.S. PATENT DOCUMENTS

| | | | |
|---|---|---|---|
| 6,232,714 B1 | 5/2001 | Shen et al. | |
| 6,245,393 B1 | 6/2001 | Thompson et al. | |
| 6,251,303 B1 | 6/2001 | Bawendi et al. | |
| 6,270,946 B1 | 8/2001 | Miller | |
| 6,319,426 B1 | 11/2001 | Bawendi et al. | |
| 6,339,227 B1 | 1/2002 | Ellenbogen | |
| 6,348,700 B1 | 2/2002 | Ellenbogen et al. | |
| 6,361,885 B1 | 3/2002 | Chou | |
| 6,365,270 B2 | 4/2002 | Forrest et al. | |
| 6,406,804 B1 | 6/2002 | Higashi et al. | |
| 6,430,511 B1 | 8/2002 | Tour et al. | |
| 6,451,455 B1 | 9/2002 | Thompson et al. | |
| 6,458,475 B1 | 10/2002 | Adachi et al. | |
| 6,479,240 B1 | 11/2002 | Kayyem et al. | |
| 6,492,096 B1 | 12/2002 | Liu et al. | |
| 6,656,608 B1 | 12/2003 | Kita et al. | |
| 6,723,455 B2 | 4/2004 | Ueda et al. | |
| 2001/0005021 A1 | 6/2001 | Fukuyama et al. | |
| 2002/0001050 A1 | 1/2002 | Pope | |
| 2002/0042174 A1 | 4/2002 | Kunugi et al. | |
| 2002/0064683 A1 | 5/2002 | Okada et al. | |
| 2002/0175619 A1 | 11/2002 | Kita et al. | |
| 2003/0087147 A1 | 5/2003 | Lee et al. | |
| 2003/0162053 A1 | 8/2003 | Marks et al. | |
| 2003/0169618 A1* | 9/2003 | Lindsey et al. | 365/151 |
| 2004/0108509 A1* | 6/2004 | Caballero | 257/88 |
| 2004/0191567 A1 | 9/2004 | Caballero | |
| 2005/0280604 A1 | 12/2005 | Caballero | |

OTHER PUBLICATIONS

B. Alpha et al., Luminescence probes: The $Eu^{3+}$-and $Tb^{3+}$-cryptates of polypyridine macrobicyclic ligands, Angew. Chem. Int. Ed. Engl. 26(12):1266-1267, 1987.

B. Alpha et al., Synthesis and characterization of the sodium and lithium cryptates of macrobicyclic ligands incorporating pyridine, bipyridine, and biisoquinoline units, Helvetica Chemica Acta 71:1042-1052, 1988.

C. D. Bain et al., Modeling organic surfaces with self-assembled monolayers, Angew. Chem. Int. Ed. Engl. 28:506-512, 1989.

C. D. Bain et al., Modeling organic surfaces with self-assembled monolayers, Adv. Mater. 4:110-116, 1989.

C. D. Bain et al., Formation of monolayer films by the spontaneous assembly of organic thiols from solution onto gold, J. Am. Chem. Soc. 111(1):321-335, 1989.

C. D. Bain et al., Formation of monolayers by the coadsorption of thiols on gold: Variation in the head group, tail group, and solvent, J. Am. Chem. Soc. 111(18):7155-7164, 1989.

S. Baroncelli et al., Light control of elongation of.filament in sunflower, Photochemistry and Photobiology 52(1):229-231, 1990.

H. Becker et al., Effect of metal films on the photoluminescence and electroluminescence of conjugated polymers, Phys. Rev. B 56(4):1893-1905, 1997.

M. L. Bhaumik et al., Studies on the triplet-triplet energy transfer to rare earth chelates, J. Phys. Chem. 69(1):275-280, 1965.

G. Blasse et al., [Eu ⊂ bpy• bpy• bpy]$^{3+}$ Cryptate: luminescence and conformation, Chem. Phys. Lett. 146(3/4):347-351, 1988.

G. Blasse et al., Luminescence processes in [Tb⊂bpy•bpy•bpy]$^{3+}$ cryptate: A low-temperature solid-state study, J. Phys. Chem. 92:2419-2422, 1988.

P. W. M. Blom et al., Device physics of polymer light-emitting diodes, Polym. Adv. Technol. 9:390-401, 1998.

A. S. Blum et al., Comparing the conductivity of molecular wires with the scanning tunneling microscope, Appl. Phys. Lett 82(19):3322-3324, 2003.

P. M. Borsenberger et al., "The role of disorder on charge transport in molecularly doped polymers and related materials," Phys. Stat. Sol (a) 140:9-47, 1993.

L. A. Bumm et al., Are single molecular wires conducting? Science 271:1705-1707, 1996.

A. J. Campbell et al., Bulk limited conduction in electroluminescent polymer devices, J. Appl. Phys. 84(12):6737-6746, 1998.

S. Capecchi et al., High-efficiency organic electroluminescent devices using an organoterbium emitter, Advanced Materials 12(21):1591-1594, 2000.

M. Carrard et al., Improved stability of interfaces in organic light emitting diodes with high $T_g$ materials and self-assembled monolayers, Thin Solid Films 352:189-194, 1999.

V. Cimrová et al., Anomalous electrical characteristics, memory phenomena and microcavity effects in polymeric light-emitting diodes, Synthetic Metals 76:125-128, 1996.

C. P. Collier et al., Electronically configurable molecular-based logic gates, Science 285:391, 1999.

G. A. Crosby et al., Intramolecular energy transfer in rare earth chelates. Role of the triplet state, J. Chem. Phys. 34(3):743-748, 1961.

G. Das et al., Facile one-pot synthesis of macrobicyclic/macrotricyclic cryptands: Effect of reactant concentrations, Tetrahedron 56:1501-1504, 2000.

W. B. Davis et al., Molecular-wire behaviour in $p$-phenylenevinylene oligomers, Nature 396:60-63, 1998.

A. A. Dhirani et al., Self-assembly of conjugated molecular rods: A high-resolution STM study, J. Am. Chem. Soc. 118:3319-3320, 1996.

L. H. Dubois et al., Synthesis, structure, and properties of model organic surfaces, Ann. Rev. Phys. Chem. 43:437-463, 1992.

K. R. Fewings et al., The synthesis and structural characterizations of some monoaza- and diaza-crown ethers, Aust. J. Chem. 52:1109-1114, 1999.

M. Fujihira et al., Growth of dark spots by interdiffusion across organic layers in organic electroluminescent devices, Appl. Phys. Lett. 68(13):1787-1789, 1996.

T. J. Gardner et al., Systems for orthogonal self-assembly of electroactive monolayers on Au and ITO: An approach to molecular electronics, J. Am. Chem. Soc. 117(26):6927-6933, 1995.

B. Gersch et al., Synthesis of new dibenzo-diaza-crown ethers, Tetrahedron Letters 37(13):2213-2216, 1996.

C. B. Gorman et al., Fabrication of patterned, electrically conducting polypyrrole using a self-assembled monolayer: A route to all-organic circuits, Chem. Mater. 7:526-529, 1995.

Y. Haas et al., Pathways of radiative and radiationless transitions in europium (III) solutions: The role of high energy vibrations, J. Phys. Chem. 75(24):3677-3681, 1971.

G. Hähner et al., Investigation of intermediate steps in the self-assembly of $n$-alkanethiols on gold surfaces by soft x-ray spectroscopy, Langmuir 9:1955-1958, 1993.

C. D. Hall et al., The synthesis and structure of a redox-active cryptand containing both aromatic and phenanthroline units within the macrocyclic structure, J. Organometallic Chem. 547:281-286, 1997.

E. M. Han et al., Study of interfacial degradation of the vapor-deposited bilayer of Alq$_3$/TPD for organic electroluminescent (EL) devices by photoluminescence, Chem. Lett. 1:57-58, 1995.

R. F. Heck, Palladium-catalyzed vinylation of organic halides, Organic Reactions 27:345-353, 1982.

W. D. Horrocks et al., Lanthanide ion luminescence probes of the structure of biological macromolecules, Acc. Chem. Res. 14:384-392, 1981.

R. P. Hsung et al., Synthesis and characterization of unsymmetric ferrocene-terminated phenylethynyl oligomers Cp$_2$Fe—[C≡C—C$_6$H$_4$]$n$—X (X=SH, SMe, SOMe, and SO$_2$Me), Organometallics 14:4808-4815, 1995.

J. Hu et al., Using soft lithography to fabricate GaAs/AlGaAs heterostructure field effect transistors, Appl. Phys. Lett. 71(14):2020-2022, 1997.

D. E. King, Oxidation of gold by ultraviolet light and ozone at 25° C, J. Vac. Sci. Technol. A13(3):1247-1253, 1995.

H. Klauk et al., Pentacene organic thin-film transistors and ICs, Solid State Technology 63-76, Mar. 2000.

K. E. Krakowiak et al., Synthesis of cryptands. A short review, Israel J. Chem. 32:3-13, 1992.

A. Kumar et al., Features of gold having micrometer to centimeter dimensions can be formed through a combination of stamping with an elastomeric stamp and an alkanethiol "ink" followed by chemical etching, Appl. Phys. Lett. 63(14):2002-2004, 1993.

A. Kumar et al., Patterning self-assembled monolayers: Applications in materials science, Langmuir 10:1498-1511, 1994.

A. Kumar et al., Patterned condensation figures as optical diffraction gratings, Science 263:60-62, 1994.

K.-Y. Law, Organic photoconductive materials: Recent trends and developments, Chem. Rev. 93:449-486, 1993.

S. T. Lee et al., Metal diffusion from electrodes in organic light-emitting diodes, Appl. Phys. Lett. 75(10):1404-1405, 1999.

J.-M. Lehn, Supramolecular chemistry—scope and perspectives. Molecules, supermolecules, and molecular devices (nobel lecture), Angew. Chem. Int. Ed. Engl. 27:89-112, 1988.

J. M. Lehn, Supramolecular chemistry—scope and perspectives: Molecules, supermolecules—molecular devices, J. Incl. Phneom. 6:351-396, 1988.

J. M. Lehn, Supramolecular Chemistry, VCH, Weimhein, Germany, pp. 1-9, 1995.

L. S. Liao et al., Bubble formation in organic light-emitting diodes, J. Appl. Phys. 88(5):2386-2390, 2000.

Z Liu et al., Efficient multilayer organic lighyt emitting diode, Synthetic Metals 122:177-179, 2001.

G. P. López et al., Fabrication and imaging of two-dimensional patterns of proteins adsorbed on self-assembled monolayers by scanning electron microscopy, J. Am. Chem. Soc. 115:10774-10781, 1993.

G. G. Malliaras et al., The roles of injection and mobility in organic light emitting diodes, J. Appl. Phys. 83(10):5399-5403, 1998.

A. R. Melnyk, Introduction to photoreceptors, IS&T's 8$^{th}$ International Congress, Advances in Non-Impact Printing Technologies, Williamsberg, VA, pp. 1-56, Oct. 25, 1992.

T. Mori et al., Effects of plasma modification on hole transport layer in organic electroluminescent diode, Jpn. J. Appl. Phys. 34(Part 2, 7A):L845-L848, 1995.

M. A. Mortellaro et al., "A turn-on for optical sensing," Chemtech 17-23, Feb. 1996.

V. P. Munk et al., Insights into the van der Waals radius of low-spin Ni(∥) from molecular mechanics studies and the crystal structures of [Ni(cis-cyclohexane-1,3-diamine)$_2$]Cl$_2$, [Ni{R)-5,5,7-trimethyl-1,4-diazacycloheptane}$_2$]Cl$_2$•H$_2$O and [Ni(5,7-dimethyl-1,4-diazacycloheptane)$_2$](ClO$_4$)$_2$. Synthesis of 5,7-dimethyl-1,4-diazacycloheptane and an improved synthesis of cis-cyclohexane-1,3-diamine, Aust. J. Chem. 55:523-529, 2002.

G. Nelles et al., Two-dimensional structure of disulfides and thiols on gold (111), Langmuir 14:808-815, 1998.

A. Nitzan et al., Electron transport in molecular wire junctions, Science 300:1384-1389, 2003.

R. G. Nuzzo et al., Adsorption of bifunctional organic disulfides on gold surfaces, J. Am. Chem. Soc. 105:4481-4484, 1993.

R. G. Nuzzo et al., Spontaneously organized molecular assemblies. 3. Preparation and properties of solution adsorbed monolayers or organic disulfides on gold surfaces, J. Am. Chem. Soc. 109:2358-2368, 1987.

R. G. Nuzzo et al., Fundamental studies of microscopic wetting on organic surfaces. 1. Formation and structural characterization of a self-consistent series of polyfunctional organic monolayers, J. Am. Chem. Soc. 112(2):558-569, 1990.

D. J. Pinner et al., Transient electroluminescence of polymer light emitting diodes using electrical pulses, J. Appl. Phys. 86(9):5116-5130, 1999.

G. E. Poirier, Characterization of organosulfur molecular monolayers on Au(111) using scanning tunneling microscopy, Chem. Rev. 97(4):1117-1127, 1997.

M. D. Porter et al., Spontaneously organized molecular assemblies. 4. Structural characterization of n-alkyl thiol monolayers on gold by optical ellipsometry, infrared spectroscopy, and electrochemistry, J. Am. Chem. Soc. 109:3559-3568, 1987.

D. Qin et al., Elastomeric light valves, Adv. Mater. 9:407-410, 1997.

G. K. Ramachandran et al., A bond-fluctuation mechanism for stochastic switching in wired molecules, Science 300:1413-1416, 2003.

D. N. Reinhoud et al., Synthesis beyond the molecule, Science 295(5564)2403-2407, 2002.

M. R. Robinson et al., Electroluminescence from well-defined tetrahedral oligophenylenevinylene tetramers, Advanced Materials 12(22):1701-1704, 2000.

J.-C. Rodrigues-Ubis et al., Synthesis of the sodium cryptates of macrobicyclic ligands containing bipyridine and phenanthroline groups, Helvetica Chemica Acta 67:2264-2269, 1984.

J. A. Rogers et al., Elastomeric diffraction gratings as photothermal detectors, Applied Optics 35(34):6641-6647, 1996.

M. G. Samant et al., An epitaxial organic film. The self-assembled monolayer of docosanoic acid on silver(111), Langmuir 9:1082-1085, 1993.

A. R. Schlatmann, Indium contamination from the indium-tin-oxide electrode in polymer light-emitting diodes, App. Phys. Lett., 69(12):1764-1766, 1996.

L. Schreyeck et al., The diaza-polyoxa-macrocycle 'Kryptofix222' as new template for the synthesis of LTA-type AlPO$_4$ co-templating role of F$^-$ and/or (CH$_3$)$_4$N$^+$ ions, Microporous and Mesoporous Materials 22:87-106, 1998.

J. C. Scott et al., Charge injection and recombination at the metal-organic interface, Chem. Phys. Lett. 299:115-119, 1999.

J. C. Scott et al., "The chemistry, physics and engineering of organic light-emitting devices," Chapter 13, In: *Semiconducting Polymers: Chemistry, Physics and Engineering*, P. G. VanHtten, G. Hadziioannou, Eds., Wiley-VCH, pp. 411-461, 1999.

Y. Shirota, Organic materials for electronic and optoelectronic devices, J. Mater. Chem. 10:1-25, 2000.

P. Sigaud et al., Determination of energy barriers in organic light-emitting diodes by internal photoemission, J. Appl. Phys. 89(1):466-470, 2001.

A. H. M. Sondag et al., Anomalous intensity effects in the IR spectrum of a densely packed monolayer of 4-acetoxybenzoic acid immobilized on oxidized aluminum. Conformational and vibrational analysis with AM1, Langmuir 8:1127-1135, 1992.

J. Spinke et al., Molecular recognition at self-assembled monolayers: Optimization of surface functionalization, J. Chem. Phys. 99(9):7012-7019, 1993.

G. Stein et al., Energy gap law in the solvent isotope effect on radiationless transitions of rare earth ions, J. Chem. Phys. 62(1):208-213, 1975.

C. Seydel, Popular Science, 35662:29, 2001.

Y.-T. Tao, Structural comparison of self-assembled monolayers of n-alkanoic acids on the surfaces of silver, copper, and aluminum, J. Am. Chem. Soc. 115:4350-4358, 1993.

N. Tessler, Transport and optical modeling of organic light-emitting diodes, Appl. Phys. Lett. 77(12):1897-1899, 2000.

S. Torii et al., Deprotection of carboxylic esters of β-lactam homologues. Cleavage of p-methoxybenzyl, diphenylmethyl, and tert-butyl esters effected by a phenolic matrix, J. Org. Chem. 56:3633-3637, 1991.

E. B. Troughton et al., Monolayer films prepared by the spontaneous self-assembly of symmetrical and unsymmetrical dialkyl sulfides from solution onto gold substrates: Structure, properties, and reactivity of constituent functional groups, Langmuir 4:365-385, 1988.

E. Tutis et al., Numerical model for organic light-emitting diodes, J. Appl. Phys. 89(1):430-439, 2001.

A. Ulman, Formation and structure of self-assembled monolayers, Chem. Rev. 96:1533-1554, 1996.

M. Weisser et al., Guest-host interactions with immobilized cyclodextrins, Sensors and Actuators B 38/39:58-67, 1997.

I. Willner et al., Application of photoisomerizable antigenic monolayer electrodes as reversible amperometric immunosensors, J. Am. Chem. Soc. 116(20):9365-9366, 1994.

U. Wolf et al., Enhanced electron injection into light-emitting diodes via interfacial tunneling, Appl. Phys. Lett. 74(25):3848-3850, 1999.

Y. Xia et al., Complex optical surfaces formed by replica molding against elastomeric masters, Science 273:347-349, 1996.

J. Xu et al., The chemistry of self-assembled long-chain alkanethiol monolayers on gold, Journal of Colloid and Interface Science 176:138-149, 1995.

J.-A. Yu et al., Direct observation of intramolecular energy transfer from a β-diketonate to terbium (III) ion encapsulated in a cryptand, Chem. Phys. Lett. 187(3):263-268, 1991.

X. Zhou et al., Communications: Real-time observation of temperature rise and thermal breakdown processes in organic LEDs using a IR imaging and analysis system, Adv. Mater. 12(4):265-273, 2000.

Y. Koide et al., "Hot microcontact printing for patterning ITO surfaces. Methodology, morphology, microstructure, and OLED charge injection barrier Imaging," Langmuir 19:86-93, 2003.

J. Shinar, Organic Light-Emitting Devices: A Survey, Chapter 1, Springer-Verlag, New York, 2004.

* cited by examiner

LIGHT EMITTING MOLECULES AND ORGANIC LIGHT EMITTING DEVICES INCLUDING LIGHT EMITTING MOLECULES

FIELD OF THE INVENTION

The invention relates to organic light emitting devices. For example, light emitting molecules and organic light emitting devices including such light emitting molecules are described.

BACKGROUND OF THE INVENTION

Organic light emitting diodes and devices (OLEDs) have begun to attract great interest for a number of applications. For example, attempts have been made to incorporate organic light emitting diodes in display devices. Organic light emitting diode devices can potentially offer a number of advantages over other types of display technologies. In particular, compared with certain types of display technologies, organic light emitting diode devices have the potential to offer lower manufacturing costs, reduced energy requirements, and improved visual characteristics.

However, existing organic light emitting devices often suffer from a number of problems. Existing organic light emitting diode devices are typically formed by depositing multiple organic layers on a substrate. The requirement of multiple organic layers can result in added weight and additional manufacturing costs. Also, the organic layers are sometimes formed from amorphous or randomly oriented polymeric materials. As a result of such random orientation, electrical conductivity of the organic layers can be inadequate, and charged species can travel in three dimensions relatively great distances along the randomly oriented polymeric materials before reaching a fluorescent or phosphorescent species that can emit light. At the same time, such random orientation can lead to the formation of "micro-wells" that can act as capacitors to further lower the electrical conductivity of the organic layers. To produce light having a desired brightness, a greater electric field density is sometimes applied to the organic layers, which electric field density can lead to thermal breakdown or instability of the organic layers. In addition, as the material draws in more current to achieve emission, UV light is emitted by the OLED material that can react with oxygen from absorbed moisture, causing radicals to form, which radicals react with the OLED material, effectively cross-linking the material, and may remove the OLED material from the surface.

U.S. Patents which illustrate various approaches to OLEDs and image display devices include e.g., U.S. Pat. No. 6,656,608 to Kita et al.; U.S. Pat. No. 6,361,885 to Chou; U.S. Pat. No. 5,677,545 to Shi et al.; U.S. Pat. No. 5,811,833 to Thompson; U.S. Pat. No. 5,946,550 to Papadimitrakopoulos; U.S. Pat. No. 6,045,930 to Thompson et al.; U.S. Pat. No. 6,251,303 to Bawendi et al.; U.S. Pat. No. 6,391,426 to Bawendi et al; U.S. Pat. No. 6,406,804 to Higashi et al.; U.S. Pat. No. 4,451,455 to Thompson et al.; U.S. Pat. No. 6,458,475 to Adachi et al.; U.S. patent application Ser. No. 2001/0005021A1 to Fukuyama et al.; U.S. patent application Ser. No. 2002/0042174 to Kunugi et al.; U.S. Pat. No. 6,030,700 to S. R. Forrest et al.; U.S. Pat. No. 6,232,714 to Shen et al.; U.S. Pat. No. 5,294,870 to C. W. Tang et al.; U.S. Pat. No. 6,245,393 to M. E. Thompson et al.; and U.S. Pat. No. 6,048,630 to Burrows et al.

References which describe various approaches to conductive organic molecules are: U.S. patent application Ser. No. 2002/0064683 to Okada et al.; U.S. Pat. No. 4,197,142 to Bolton et al.; U.S. Pat. No. 6,492,096 to Liu et al.; U.S. Pat. No. 6,479,240 to Kayyem et al.; U.S. Pat. No. 6,430,511 to Tour et al.; U.S. Pat. No. 6,348,700 to Ellenbogen et al.; U.S. Pat. No. 6,339,227 to Ellenbogen et al.; U.S. Pat. No. 6,169,291 to Metzger et al.; U.S. Pat. No. 6,096,273 to Kayyem et al.; U.S. Pat. No. 6,060,327 to Keen et al.; U.S. Pat. No. 6,028,265 to Ono et al.; U.S. Pat. No. 5,525,811 to Sakurai et al.; U.S. Pat. No. 5,057,878 to Geddes et al.; U.S. Pat. No. 5,010,451 to Ueyama et al; Liu, et al. Synthetic Metals, 122 (2001) 177-179; Ramachandran, et al., Science, 300 (2003) 1413-1416; Blum, et al. Appl. Phys. Lett. 82 (2003) 3322-3324; Nitzan, et al., Science 300 (2003), 1384-1389.

It is against this background that a need arose to develop the light emitting molecules and organic light emitting devices described herein.

SUMMARY OF THE INVENTION

In one aspect, the invention relates to a light emitting molecule. In one embodiment, the light emitting molecule comprises an anchoring group and a charge transport group having a first end and a second end. The first end of the charge transport group is bonded to the anchoring group. The charge transport group allows transport of electrical energy. The transport of electrical energy can be one- or two- dimensional. One dimensional transport of electrical energy occurs when electrical energy travels along the light emitting molecule. Two-dimensional transport of electrical energy occurs when electrical energy travels between portions of different light emitting molecules, for example, charge transport groups of two different light emitting molecules. Travel of electrical energy between light emitting molecules can occur when portions of two different light emitting molecules, for example, charge transport groups interact (for example, are linked together). Two-dimensional transport of electrical energy allows electrical energy transfer to occur even if a defect is present in a layer of light emitting molecules. The light emitting molecule also comprises a light emissive group bonded to the second end of the charge transport group and a charge transfer group bonded to the light emissive group. A light emitting molecule can include one or more charge transport groups and one or more light emissive groups. A light emitting molecule can include one or more charge transfer groups. The one or more charge transport groups can be configured to provide transport of electrical energy to the one or more light emissive groups. In some instances, the transport of electrical energy can be substantially one-dimensional, such as, for example, along a longitudinal axis of a charge transport group. The one or more light emissive groups can be configured to emit light having a desired wavelength or range of wavelengths. In one embodiment, there may be more than one wavelength emitted from the same light emitting molecule. In one embodiment, the anchoring group is covalently bound to a surface.

In one embodiment, the charge transport group is a conjugated group extending from the anchoring group, said conjugated group having a first end bonded to the anchoring group and said conjugated group having a second end. A light emissive group is bonded to the second end of the conjugated group. In one embodiment, the conjugated group has formula $(A-B)_m$-A, m being an integer typically in the range of 1 to about 20 more typically in the range of 2 to about 5, A being an arylene group, B being one of an alkenylene group, an alkynylene group, and an iminylene group. Other embodiments of conjugated groups and charge transport groups are discussed below.

In another aspect, the invention relates to a pixel or a pixel element. A pixel is a separately electrically addressable pixel element. A pixel element comprises one or more light emitting molecules that can be the same or different. In one embodiment, a pixel element comprises one or more of the same light emitting molecules. In another embodiment, the pixel element comprises one or more different light emitting molecules (which may emit light at the same or different wavelengths). In yet another aspect, the invention relates to an organic light emitting device. An organic light emitting device comprises one or more pixel elements comprising one or more light emitting molecules, as described herein. In some instances, the one or more light emitting molecules are substantially aligned with respect to a common direction, and each light emitting molecule of the pixel elements extends between the two conductive layers. In one embodiment, the organic light emitting device comprises one or more pixel elements. The pixel elements may be arranged in an array. At least one pixel element of the one or more pixel elements comprises one or more light emitting molecules as described herein, wherein the anchoring group is configured to bond the light emitting molecule to a first conductive layer and the charge transfer group is configured to bond the light emitting molecule to a second conductive layer. In specific embodiments the anchoring group bonds the light emitting molecule to the conductive layer through one or more chemical bonds, particularly through one or more covalent bonds.

In a further aspect, the invention relates to a display device. In one embodiment, the display device comprises two conductive layers, for example, an anode layer and a cathode layer, and one or more pixel elements positioned between the two conductive layers. The pixel elements may be arranged in an array. At least one pixel element of the one or more pixel elements comprises one or more light emitting molecules that comprises an anchoring group bonded to the first conductive layer and a charge transport group bonded to the second conductive layer. Preferably, the anchoring group is covalently bound to the anode layer and the charge transfer group is bonded to the cathode layer.

In another embodiment, the display device comprises a first conductive layer, a second conductive layer, and one or more light emitting molecules positioned between the first conductive layer and the second conductive layer. In one embodiment, the one or more light emitting molecules are substantially aligned with respect to a common direction (meaning more molecules are aligned with respect to the common direction than molecules that are not aligned with respect to the common direction). In one embodiment, at least one light emitting molecule of the one or more light emitting molecules comprises an anchoring group bonded to the first conductive layer, a conjugated group extending from the anchoring group and having a first end bonded to the anchoring group and a second end, where a light emissive group is bonded to the second end of the conjugated group and the light emitting molecule is in electrical connection with the second conductive layer.

BRIEF DESCRIPTION OF THE DRAWINGS

For a further understanding of the nature and objects of various embodiments of the invention, reference is made to the following detailed description in conjunction with the accompanying drawings.

DETAILED DESCRIPTION

Figure 1:
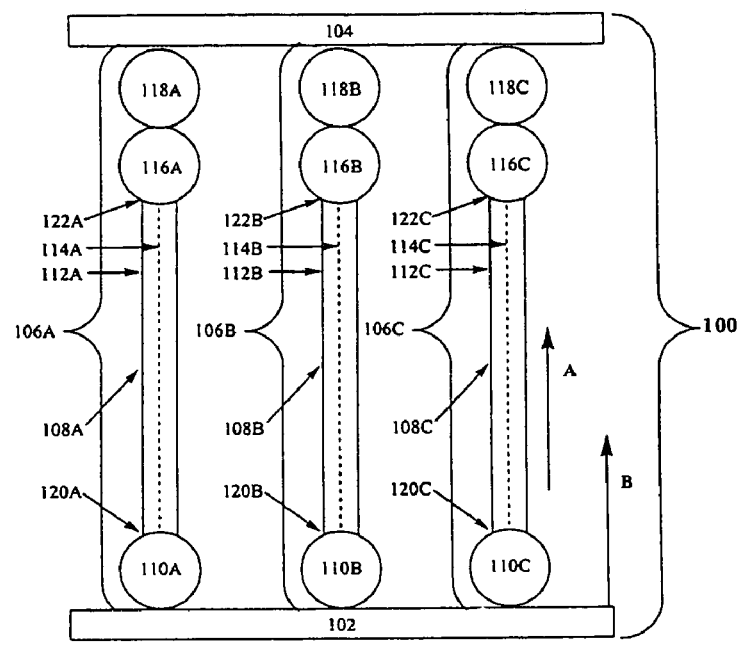
FIG. 1 illustrates a side sectional view of an organic light emitting device according to an embodiment of the invention.

Various embodiments of the invention relate to light emitting molecules and organic light emitting devices including such light emitting molecules. Organic light emitting devices in accordance with various embodiments of the invention can offer a number of advantages, such as, for example, improved transport of electrical energy, improved robustness and thermal stability, improved visual characteristics, reduced energy requirements, reduced weight and lower manufacturing costs.

DEFINITIONS

The following definitions apply to some of the elements described with regard to some embodiments of the invention. These definitions may likewise be expanded upon herein.

As used herein, "array" means an arrangement of more than one light emitting molecule or pixel element. Arrays can be ordered, where the relative spacing between light emitting molecules or pixel elements and/or relative alignment of light emitting molecules or pixel elements has been selected for a particular application. The array can have a regular order so that the relative spacing and/or relative alignment are substantially similar. Arrays can also have relative spacing and/or relative alignment of light emitting molecules that is not regular. The light emitting molecules in an array may be the same or different. Similarly, arrays can comprise more than one pixel element comprising the same light emitting molecules, or can comprise more than one pixel element comprising different light emitting molecules.

As used herein, "light emitting molecule" includes pre-light emitting molecules, those molecules which are capable of binding a luminescer and emitting light upon application of a suitable stimulus such as light or energy application. "Light emitting molecule" also includes molecules that are capable of emitting light upon application of a suitable stimulus such as light or energy application without binding a luminescer, for example, those light emitting molecules that include a luminescer. "Light emissive group" includes pre-light emissive groups, those groups which are capable of binding a luminescer and emitting light upon application of a suitable stimulus such as light or energy application. "Light emissive group" also includes groups that are capable of emitting light upon application of a suitable stimulus such as light or energy application, for example, those light emissive groups that include a luminescer.

As used herein, light emission means emission of any wavelength of light.

Preferably, light emission means light that is detectable in the visible wavelength range. Preferably, light emission means light that is observable by the human eye (generally from 400 to 750 nm). Preferred visible wavelength ranges include those wavelengths that emit in the red color family (from 650 to 750 nm), the blue color family (from 435 to 500 nm) and the green color family (from 500 to 560 nm). Other regions of the spectrum and other colors are included in the term light emission. As described herein and known to one of ordinary skill in the art, the selection of the luminescer affects the wavelength of emission.

As used herein, "substantially" means more of the given structures have the listed property than do not have the listed property. For example, as used herein, "substantially aligned molecules" means at least 50% of molecules in a group are aligned in a given direction.

As used herein, "substitution group" includes those groups commonly known in the art as "substituent" groups or groups that are added to a chemical structure.

As used herein, "configured to bond" means able to form a bond as defined herein.

As used herein, "anode layer" means a negatively charged group or surface. As used herein, "cathode layer" means a positively charged group or surface. As used herein, "conductive layer" means a layer which can conduct electrical energy, for example an anode layer or cathode layer.

The term "set" refers to a collection of one or more elements. Elements of a set can also be referred to as members of the set. Elements of a set can be the same or different. In some instances, elements of a set can share one or more common characteristics.

The term "bond" and its grammatical variations refer to a coupling or joining of two or more chemical or physical elements. In some instances, a bond can refer to a coupling of two or more atoms based on an attractive interaction, such that these atoms can form a stable structure. Examples of bonds include chemical bonds such as chemisorptive bonds, covalent bonds, ionic bonds, van der Waals bonds, and hydrogen bonds. The term "intermolecular bond" refers to a chemical bond between two or more atoms that form different molecules, while the term "intramolecular bond" refers to a chemical bond between two or more atoms in a single molecule, such as, for example, a chemical bond between two groups of the single molecule.

Typically, an intramolecular bond includes one or more covalent bonds, such as, for example, σ-bonds, π-bonds, and coordination bonds. The term "conjugated π-bond" refers to a π-bond that has a π-orbital overlapping (e.g., substantially overlapping) a π-orbital of an adjacent π-bond. Additional examples of bonds include various mechanical, physical, and electrical couplings.

The term "group" as applies to chemical species refers to a set of atoms that form a portion of a molecule. In some instances, a group can include two or more atoms that are bonded to one another to form a portion of a molecule. A group can be monovalent or polyvalent (e.g., bivalent) to allow bonding to one or more additional groups of a molecule. For example, a monovalent group can be envisioned as a molecule with one of its hydrogen atoms removed to allow bonding to another group of a molecule. A group can be positively or negatively charged.

For example, a positively charged group can be envisioned as a neutral group with one or more protons (i.e., H+) added, and a negatively charged group can be envisioned as a neutral group with one or more protons removed. Examples of groups include alkyl groups, alkylene groups, alkenyl groups, alkenylene groups, alkynyl groups, alkynylene groups, aryl groups, arylene groups, iminyl groups, iminylene groups, hydride groups, halo groups, hydroxy groups, alkoxy groups, carboxy groups, thio groups, alkylthio groups, disulfide groups, cyano groups, nitro groups, amino groups, alkylamino groups, dialkylamino groups, silyl groups, and siloxy groups.

The term "conjugated group" refers to a group that includes a set of conjugated π-bonds. Typically, a set of conjugated π-bonds can extend through at least a portion of a length of a conjugated group. In some instances, a set of conjugated π-bonds can substantially extend through a length of a conjugated group. In other instances, a set of conjugated π-bonds can include one or more non-conjugated portions, such as, for example, one or more portions lacking substantial overlapping of π-orbitals. Examples of groups that can be used to form a conjugated group include alkylene groups, alkenylene groups, alkynylene groups, arylene groups, and iminylene groups. A conjugated group can be formed from a single group that includes a set of conjugated π-bonds. Alternatively, a conjugated group can be formed from multiple groups that are bonded to one another to provide a set of conjugated π-bonds. A conjugated group can contain ring structures or linear structures, or a combination of both. A conjugated group can, for example, be formed from a combination of one or more arylene groups and one or more alkenylene groups, alkynylene groups or iminylene groups. A conjugated group can include one or more of the groups shown in Scheme B, for example. A conjugated group can contain multiple groups that can be the same or different.

For example, a conjugated group can be formed from n arylene groups, where n is an integer that can be, for example, in the range of 2 to 20. The n arylene groups can be bonded to one another to form a chain structure, and the n arylene groups can include a single type of arylene group or multiple types of arylene groups. In some instances, each arylene group can be independently selected from lower arylene groups, upper arylene groups, monocyclic arylene groups, polycyclic arylene groups, heteroarylene groups, substituted arylene groups, and unsubstituted arylene groups. Each successive pair of arylene groups of the chain structure can be bonded to one another via a group that can be independently selected from alkenylene groups, alkynylene groups, and iminylene groups. For example, the conjugated group can be formed from n alkenylene groups, and the n alkenylene groups can include a single type of alkenylene group or multiple types of alkenylene groups. In some instances, each alkenylene group can be bonded to two successive arylene groups of the chain structure and can be independently selected from lower alkenylene groups, upper alkenylene groups, cycloalkenylene groups, heteroalkenylene groups, substituted alkenylene groups, and unsubstituted alkenylene groups. As another example, the conjugated group can be formed from n alkynylene groups that can be the same or different, and each alkynylene group can be bonded to two successive arylene groups of the chain structure. As a further example, the conjugated group can be formed from n iminylene groups that can be the same or different, and each iminylene group can be bonded to two successive arylene groups of the chain structure.

The term "electron accepting group" refers to a group that has a tendency to attract an electron from another group of the same or a different molecule. The term "electron donating group" refers to a group that has a tendency to provide an electron to another group of the same or a different molecule.

For example, an electron accepting group can have a tendency to attract an electron from an electron donating group that is bonded to the electron accepting group. It should be recognized that electron accepting and electron providing characteristics of a group are relative. In particular, a group that serves as an electron accepting group in one molecule can serve as an electron donating group in another molecule. Examples of electron accepting groups include positively charged groups and groups including atoms with relatively high electronegativities, such as, for example, halo groups, hydroxy groups, cyano groups, and nitro groups. Examples of electron donating groups include negatively charged groups and groups including atoms with relatively low electronegativities, such as, for example, alkyl groups.

The term "alkane" refers to a saturated hydrocarbon molecule. For certain applications, an alkane can include from 1 to 100 carbon atoms. The term "lower alkane" refers to an alkane that includes from 1 to 20 carbon atoms, such as, for example, from 1 to 10 carbon atoms, while the term "upper alkane" refers to an alkane that includes more than 20 carbon atoms, such as, for example, from 21 to 100 carbon atoms. The term "small alkane" refers to an alkane having from 1 to 6 carbon atoms. The term "branched alkane" refers to an alkane that includes one or more branches, while the term "unbranched alkane" refers to an alkane that is straight-chained. The term "cycloalkane" refers to an alkane that includes one or more ring structures. The term "heteroalkane" refers to an alkane that has one or more of its carbon atoms replaced by one or more heteroatoms, such as, for example, N, Si, S, O, and P. The term "substituted alkane" refers to an alkane that has one or more of its hydrogen atoms replaced by one or more substituent groups, such as, for example, halo groups, hydroxy groups, alkoxy groups, carboxy groups, thio groups, alkylthio groups, cyano groups, nitro groups, amino groups, alkylamino groups, dialkylamino groups, silyl groups, and siloxy groups, while the term "unsubstituted alkane" refers to an alkane that lacks such substituent groups. Combinations of the above terms can be used to refer to an alkane having a combination of characteristics. For example, the term "branched lower alkane" can be used to refer to an alkane that includes from 1 to 20 carbon atoms and one or more branches. Examples of alkanes include methane, ethane, propane, cyclopropane, butane, 2-methylpropane, cyclobutane, and charged, hetero, or substituted forms thereof.

The term "alkyl group" refers to a monovalent form of an alkane. For example, an alkyl group can be envisioned as an alkane with one of its hydrogen atoms removed to allow bonding to another group of a molecule. The term "lower alkyl group" refers to a monovalent form of a lower alkane, while the term "upper alkyl group" refers to a monovalent form of an upper alkane. The term "branched alkyl group" refers to a monovalent form of a branched alkane, while the term "unbranched alkyl group" refers to a monovalent form of an unbranched alkane. The term "small alkyl group" refers to a monovalent form of a small alkane. The term "cycloalkyl group" refers to a monovalent form of a cycloalkane, and the term "heteroalkyl group" refers to a monovalent form of a heteroalkane. The term "substituted alkyl group" refers to a monovalent form of a substituted alkane, while the term "unsubstituted alkyl group" refers to a monovalent form of an unsubstituted alkane. Examples of alkyl groups include methyl, ethyl, n-propyl, isopropyl, cyclopropyl, butyl, isobutyl, t-butyl, cyclobutyl, and charged, hetero, or substituted forms thereof.

The term "alkylene group" refers to a bivalent form of an alkane. For example, an alkylene group can be envisioned as an alkane with two of its hydrogen atoms removed to allow bonding to one or more additional groups of a molecule. The term "lower alkylene group" refers to a bivalent form of a lower alkane, while the term "upper alkylene group" refers to a bivalent form of an upper alkane. The term "small alkylene group" refers to a bivalent form of a small alkane. The term "branched alkylene group" refers to a bivalent form of a branched alkane, while the term "unbranched alkylene group" refers to a bivalent form of an unbranched alkane. The term "cycloalkylene group" refers to a bivalent form of a cycloalkane, and the term "heteroalkylene group" refers to a bivalent form of a heteroalkane. The term "substituted alkylene group" refers to a bivalent form of a substituted alkane, while the term "unsubstituted alkylene group" refers to a bivalent form of an unsubstituted alkane. Examples of alkylene groups include methylene, ethylene, propylene, 2-methylpropylene, and charged, hetero, or substituted forms thereof.

The term "alkene" refers to an unsaturated hydrocarbon molecule that includes one or more carbon-carbon double bonds. For certain applications, an alkene can include from 2 to 100 carbon atoms. The term "lower alkene" refers to an alkene that includes from 2 to 20 carbon atoms, such as, for example, from 2 to 10 carbon atoms, while the term "upper alkene" refers to an alkene that includes more than 20 carbon atoms, such as, for example, from 21 to 100 carbon atoms. The term "small alkene" refers to an alkene group that includes from 1 to 6 carbon atoms. The term "cycloalkene" refers to an alkene that includes one or more ring structures. The term "heteroalkene" refers to an alkene that has one or more of its carbon atoms replaced by one or more heteroatoms, such as, for example, N, Si, S, O, and P. The term "substituted alkene" refers to an alkene that has one or more of its hydrogen atoms replaced by one or more substituent groups, such as, for example, alkyl groups, halo groups, hydroxy groups, alkoxy groups, carboxy groups, thio groups, alkylthio groups, cyano groups, nitro groups, amino groups, alkylamino groups, dialkylamino groups, silyl groups, and siloxy groups, while the term "unsubstituted alkene" refers to an alkene that lacks such substituent groups. Combinations of the above terms can be used to refer to an alkene having a combination of characteristics. For example, the term "substituted lower alkene" can be used to refer to an alkene that includes from 1 to 20 carbon atoms and one or more substituent groups. Examples of alkenes include ethene, propene, cyclopropene, 1-butene, trans-2 butene, cis-2-butene, 1,3-butadiene, 2-methylpropene, cyclobutene, and charged, hetero, or substituted forms thereof.

The term "alkenyl group" refers to a monovalent form of an alkene. For example, an alkenyl group can be envisioned as an alkene with one of its hydrogen atoms removed to allow bonding to another group of a molecule. The term "lower alkenyl group" refers to a monovalent form of a lower alkene, while the term "upper alkenyl group" refers to a monovalent form of an upper alkene. The term "small alkenyl group" refers to a monovalent form of a small alkene. The term "cycloalkenyl group" refers to a monovalent form of a cycloalkene, and the term "heteroalkenyl group" refers to a monovalent form of a heteroalkene. The term "substituted alkenyl group" refers to a monovalent form of a substituted alkene, while the term "unsubstituted alkenyl group" refers to a monovalent form of an unsubstituted alkene. Examples of alkenyl groups include ethenyl, propenyl, isopropenyl, cyclopropenyl, butenyl, isobutenyl, t-butenyl, cyclobutenyl, and charged, hetero, or substituted forms thereof.

The term "alkenylene group" refers to a bivalent form of an alkene. For example, an alkenylene group can be envisioned as an alkene with two of its hydrogen atoms removed to allow bonding to one or more additional groups of a molecule. The term "lower alkenylene group" refers to a bivalent form of a lower alkene, while the term "upper alkenylene group" refers to a bivalent form of an upper alkene. The term "small alkenylene group" refers to a bivalent form of a small alkene. The term "cycloalkenylene group" refers to a bivalent form of a cycloalkene, and the term "heteroalkenylene group" refers to a bivalent form of a heteroalkene.

The term "substituted, alkenylene group" refers to a bivalent form of a substituted alkene, while the term "unsubstituted alkenylene group" refers to a bivalent form of an unsubstituted alkene. Examples of alkenyl groups include ethenylene, propenylene, 2-methylpropenylene, and charged, hetero, or substituted forms thereof.

The term "alkyne" refers to an unsaturated hydrocarbon molecule that includes one or more carbon-carbon triple bonds. In some instances, an alkyne can also include one or more carbon-carbon double bonds. For certain applications, an alkyne can include from 1 to 100 carbon atoms. The term "lower alkyne" refers to an alkyne that includes from 2 to 20 carbon atoms, such as, for example, from 2 to 10 carbon atoms, while the term "upper alkyne" refers to an alkyne that includes more than 20 carbon atoms, such as, for example, from 21 to 100 carbon atoms. The term "small alkyne" refers to an alkyne group that includes from 1 to 6 carbon atoms. The term "cycloalkyne" refers to an alkyne that includes one or more ring structures. The term "heteroalkyne" refers to an alkyne that has one or more of its carbon atoms replaced by one or more heteroatoms, such as, for example, N, Si, S, O, and P. The term "substituted alkyne" refers to an alkyne that has one or more of its hydrogen atoms replaced by one or more substituent groups, such as, for example, alkyl groups, alkenyl groups, halo groups, hydroxy groups, alkoxy groups, carboxy groups, thio groups, alkylthio groups, cyano groups, nitro groups, amino groups, alkylamino groups, dialkylamino groups, silyl groups, and siloxy groups, while the term "unsubstituted alkyne" refers to an alkyne that lacks such substituent groups. Combinations of the above terms can be used to refer to an alkyne having a combination of characteristics. For example, the term "substituted lower alkyne" can be used to refer to an alkyne that includes from 1 to 20 carbon atoms and one or more substituent groups. Examples of alkynes include ethyne (i.e., acetylene), propyne, 1-butyne, 1-buten-3-yne, 1-pentyne, 2-pentyne, 3-penten-1-yne, 1-penten-4-yne, 3-methyl-1-butyne, and charged, hetero, or substituted forms thereof.

The term "alkynyl group" refers to a monovalent form of an alkyne. For example, an alkynyl group can be envisioned as an alkyne with one of its hydrogen atoms removed to allow bonding to another group of a molecule. The term "lower alkynyl group" refers to a monovalent form of a lower alkyne, while the term "upper alkynyl group" refers to a monovalent form of an upper alkyne. The term "small alkynyl group" refers to a monovalent form of a small alkyne. The term "cycloalkynyl group" refers to a monovalent form of a cycloalkyne, and the term "heteroalkynyl group" refers to a monovalent form of a heteroalkyne. The term "substituted alkynyl group" refers to a monovalent form of a substituted alkyne, while the term "unsubstituted alkynyl group" refers to a monovalent form of an unsubstituted alkyne. Examples of alkynyl groups include ethynyl, propynyl, isopropynyl, butynyl, isobutynyl, t-butynyl, and charged, hetero, or substituted forms thereof.

The term "alkynylene group" refers to a bivalent form of an alkyne. For example, an alkynylene group can be envisioned as an alkyne with two of its hydrogen atoms removed to allow bonding to one or more additional groups of a molecule. The term "lower alkynylene group" refers to a bivalent form of a lower alkyne, while the term "upper alkynylene group" refers to a bivalent form of an upper alkyne. The term "small alkynylene group" refers to a bivalent form of a small alkyne. The term "cycloalkynylene group" refers to a bivalent form of a cycloalkyne, and the term "heteroalkynylene group" refers to a bivalent form of a heteroalkyne. The term "substituted alkynylene group" refers to a bivalent form of a substituted alkyne, while the term "unsubstituted alkynylene group" refers to a bivalent form of an unsubstituted alkyne. Examples of alkynylene groups include ethynylene, propynylene, 1-butynylene, 1-buten-3-ynylene, and charged, hetero, or substituted forms thereof.

The term "arene" refers to an aromatic hydrocarbon molecule. For certain applications, an arene can include from 5 to 100 carbon atoms. The term "lower arene" refers to an arene that includes from 5 to 20 carbon atoms, such as, for example, from 5 to 14 carbon atoms, while the term "upper arene" refers to an arene that includes more than 20 carbon atoms, such as, for example, from 21 to 100 carbon atoms. The term "small arene" refers to an arene group that includes from 5-7 carbon atoms. The term "monocyclic arene" refers to an arene that includes a single aromatic ring structure, while the term "polycyclic arene" refers to an arene that includes more than one aromatic ring structure, such as, for example, two or more aromatic ring structures that are bonded via a carbon-carbon single bond or that are fused together. The term "heteroarene" refers to an arene that has one or more of its carbon atoms replaced by one or more heteroatoms, such as, for example, N, Si, S, O, and P. The term "substituted arene" refers to an arene that has one or more of its hydrogen atoms replaced by one or more substituent groups, such as, for example, alkyl groups, alkenyl groups, alkynyl groups, iminyl groups, halo groups, hydroxy groups, alkoxy groups, carboxy groups, thio groups, alkylthio groups, cyano groups, nitro groups, amino groups, alkylamino groups, dialkylamino groups, silyl groups, and siloxy groups, while the term "unsubstituted arene" refers to an arene that lacks such substituent groups. Combinations of the above terms can be used to refer to an arene having a combination of characteristics. For example, the term "monocyclic lower alkene" can be used to refer to an arene that includes from 5 to 20 carbon atoms and a single aromatic ring structure. Examples of arenes include benzene, biphenyl, naphthalene, pyridine, pyridazine, pyrimidine, pyrazine, quinoline, isoquinoline, and charged, hetero, or substituted forms thereof.

The term "aryl group" refers to a monovalent form of an arene. For example, an aryl group can be envisioned as an arene with one of its hydrogen atoms removed to allow bonding to another group of a molecule. The term "lower aryl group" refers to a monovalent form of a lower arene, while the term "upper aryl group" refers to a monovalent form of an upper arene. The term "small aryl group" refers to a monovalent form of a small arene. The term "monocyclic aryl group" refers to a monovalent form of a monocyclic arene, while the term "polycyclic aryl group" refers to a monovalent form of a polycyclic arene. The term "heteroaryl group" refers to a monovalent form of a heteroarene. The term "substituted aryl group" refers to a monovalent form of a substituted arene, while the term "unsubstituted arene group" refers to a monovalent form of an unsubstituted arene. Examples of aryl groups include phenyl, biphenylyl, naphthyl, pyridinyl, pyridazinyl, pyrimidinyl, pyrazinyl, quinolyl, isoquinolyl, and charged, hetero, or substituted forms thereof.

The term "arylene group" refers to a bivalent form of an arene. For example, an arylene group can be envisioned as an arene with two of its hydrogen atoms removed to allow bonding to one or more additional groups of a molecule. The term "lower arylene group" refers to a bivalent form of a lower arene, while the term "upper arylene group" refers to a bivalent form of an upper arene. The term "small arylene group" refers to a bivalent form of a small arene. The term "monocyclic arylene group" refers to a bivalent form of a monocyclic arene, while theterm "polycyclic arylene group" refers to a bivalent form of a polycyclic arene. The term "heteroarylene group" refers to a bivalent form of a heteroarene. The term "substituted arylene group" refers to a bivalent form of a substituted arene, while the term "unsubstituted arylene group" refers to a bivalent form of an unsubstituted arene. Examples of arylene groups include phenylene, biphenylylene, naphthylene, pyridinylene, pyridazinylene, pyrimidinylene, pyrazinylene, quinolylene, isoquinolylene, and charged, hetero, or substituted forms thereof.

The term "imine" refers to a molecule that includes one or more carbon-nitrogen double bonds. For certain applications, an imine can include from 1 to 100 carbon atoms. The term "lower imine" refers to an imine that includes from 1 to 20 carbon atoms, such as, for example, from 1 to 10 carbon atoms, while the term "upper imine" refers to an imine that includes more than 20 carbon atoms, such as, for example, from 21 to 100 carbon atoms. The term "small imine" refers to an imine that has from 1 to 6 carbon atoms. The term "cycloimine" refers to an imine that includes one or more ring structures. The term "heteroimine" refers to an imine that has one or more of its carbon atoms replaced by one or more heteroatoms, such as, for example, N, Si, S, O, and P. The term "substituted imine" refers to an imine that has one or more of its hydrogen atoms replaced by one or more substituent groups, such as, for example, alkyl groups, alkenyl groups, alkynyl groups, halo groups, hydroxy groups, alkoxy groups, carboxy groups, thio groups, alkylthio groups, cyano groups, nitro groups, amino groups, alkylamino groups, dialkylamino groups, silyl groups, and siloxy groups, while the term "unsubstituted imine" refers to an imine that lacks such substituent groups. Combinations of the above terms can be used to refer to an imine having a combination of characteristics. For example, the term "substituted lower imine" can be used to refer to an imine that includes from 1 to 20 carbon atoms and one or more substituent groups. Examples of imines include $R^aCH=NR^b$, where $R^a$ and $R^b$ are independently selected from hydride groups, alkyl groups, alkenyl groups, and alkynyl groups.

The term "iminyl group" refers to a monovalent form of an imine. For example, an iminyl group can be envisioned as an imine with one of its hydrogen atoms removed to allow bonding to another group of a molecule. The term "lower iminyl group" refers to a monovalent form of a lower imine, while the term "upper iminyl group" refers to a monovalent form of an upper imine. The term "small iminyl group" refers to a monovalent form of a small imine. The term "cycloiminyl group" refers to a monovalent form of a cycloimine, and the term "heteroiminyl group" refers to a monovalent form of a heteroimine. The term "substituted iminyl group" refers to a monovalent form of a substituted imine, while the term "unsubstituted iminyl group" refers to a monovalent form of an unsubstituted imine. Examples of iminyl groups include $-R^cCH=NR^d$, $R^eCH=NR^f-$, $-CH=NR^g$, and $R^hCH=N-$, where $R^c$ and $R^f$ are independently selected from alkylene groups, alkenylene groups, and alkynylene groups, and $R^d$, $R^e$, $R^g$, and $R^h$ are independently selected from hydride groups, halo groups, alkyl groups, alkenyl groups, and alkynyl groups.

The term "iminylene group" refers to a bivalent form of an imine. For example, an iminylene group can be envisioned as an imine with two of its hydrogen atoms removed to allow bonding to one or more additional groups of a molecule. The term "lower iminylene group" refers to a bivalent form of a lower imine, while the term "upper iminylene group" refers to a bivalent form of an upper imine. The term "small iminylene group" refers to a bivalent form of a small imine. The term "cycloiminylene group" refers to a bivalent form of a cycloimine, and the term "heteroiminylene group" refers to a bivalent form of a heteroimine. The term "substituted iminylene group" refers to a bivalent form of a substituted imine, while the term "unsubstituted iminylene group" refers to a bivalent form of an unsubstituted imine. Examples of iminylene groups include $-R^iCH=NR^j-$, $-CH=NR^k-$, $-R^lCH=N-$, and $-CH=N-$, where $R^i$, $R^j$, $R^k$, and $R^l$ are independently selected from alkylene groups, alkenylene groups, and alkynylene groups.

The term "hydride group" refers to $-H$, which may be negatively charged

The term "halo group" refers to $-X$, where X is a halogen atom. Examples of halo groups include fluoro, chloro, bromo, and iodo.

The term "hydroxy group" refers to $-OH$.

The term "alkoxy group" refers to $-OR^m$, where $R^m$ is an alkyl group. Examples of alkoxy groups include methoxy, ethoxy, propoxy, isopropoxy, and charged, hetero, or substituted forms thereof.

The term "carboxy group" refers to $-COOH$.

The term "thio group" refers to $-SH$.

The term "alkylthio group" refers to a $-SR^n$, where $R^n$ is an alkyl group. Examples of alkylthio groups include methylthio, ethylthio, propylthio, isopropylthio, and charged, hetero, or substituted forms thereof.

The term "disulfide group" refers to $-S-S-$.

The term "cyano group" refers to $-CN$.

The term "nitro group" refers to $-NO_2$.

The term "amino group" refers to $-NH_2$.

The term "alkylamino group" refers to $-NHR^o$, where $R^o$ is an alkyl group. Examples of alkylamino groups include methylamino, ethylamino, propylamino, isopropylamino, and charged, hetero, or substituted forms thereof.

The term "dialkylamino group" refers to $-NR^pR^q$, where $R^p$ and $R^q$ are independently selected from alkyl groups. Examples of dialkylamino groups include dimethylamino, methylethylamino, diethylamino, dipropylamino, and charged, hetero, or substituted forms thereof.

The term "silyl group" refers to $-SiR^rR^sR^t$, where $R^r$, $R^s$, and $R^t$ are independently selected from a number of groups, such as, for example, hydride groups, halo groups, alkyl groups, alkenyl groups, and alkynyl groups. Examples of silyl groups include trimethylsilyl, dimethylethylsilyl, diethylmethylsilyl, triethylsilyl, and charged, hetero, or substituted forms thereof. The term "siloxy group" refers to $-O-SiR^uR^vR^w$, where $R^u$, $R^v$, and $R^w$ are independently selected from a number of groups, such as, for example, hydride groups, halo groups, alkyl groups, alkenyl groups, and alkynyl groups. Examples of siloxy groups include trimethylsiloxy, dimethylethylsiloxy, diethylmethylsiloxy, triethylsiloxy, and charged, hetero, or substituted forms thereof.

The term "silane" refers to a chemical structure based on $SiH_4$, where one or more of the hydrogens may be replaced with any group that binds to the silicon atom, such as halogen, oxygen, alkyl groups, alkenyl groups, and alkynyl groups.

The term "luminescer" refers to one or more atoms configured to emit light in response to an energy excitation. In some instances, a luminescer can form a portion of a molecule. A luminescer can emit light in accordance with a number of mechanisms, such as, for example, chemiluminescence, electroluminescence, photoluminescence, and combinations thereof. For example, a luminescer can exhibit photoluminescence in accordance with an absorption-energy transfer-emission mechanism, fluorescence, or phosphorescence. In some instances, a luminescer can be selected based on a desired wavelength or range of wavelengths of light emitted by the luminescer. Examples of luminescers include organic fluorescers, semiconductor nanocrystals, chromophores, including metal-containing chromophores and nonmetal-containing chromophores. Thus, for certain applications, a luminescer can include a metal atom, such as, for example, a transition metal atom or a lanthanide metal atom. Examples of transition metals atoms include Cd, Cu, Co, Pd, Zn, Fe, Ru, Rh, Os, Re, Pt, Sc, Ti, V, Cr, Mn, Ni, Mo, Tc, W, La, and Ir. Examples of lanthanide metal atoms include Nd, Pm, Sm, Eu, Gd, Dy, Tb, Ho, Er, Tm, Yb, and Lu. Any individual metal or subset of metals listed are included in the disclosure. Typically, a metal atom that is part of a luminescer is positively charged and is provided in the form of a metal ion. As known in the art, the oxidation state of the metal ion depends on the species around it, and the metal ion can have a variety of charges, for example +3, +2, +1, etc.

The term "ligand" refers to one or more atoms configured to bond to a target. In some instances, a ligand can form a portion of a molecule. A ligand can be configured to bond to a luminescer to form a ligand-luminescer complex. A ligand can include a set of coordination atoms to allow bonding to a luminescer. Examples of coordination atoms that can form coordination bonds with a luminescer include N, C, Si, S, O, P, and halogens. In particular, halogens can act as coordination donors to the ligated metal. Halogens can displace water, but can result in a longer time of emission, as known in the art. In some instances, the number and type of coordination atoms can depend on a particular luminescer to be bonded. For certain applications, the number and type of coordination atoms can be selected based on a coordination number of a metal ion. For example, when a metal ion has a coordination number of 9, a ligand can include up to 9 coordination atoms to allow bonding to the metal ion. Ligands can be multidentate. A ligand can be monocyclic (i.e., include a single ring structure) or polycyclic (i.e., include more than one ring structure). In some instances, a ligand can encage a luminescer within a cavity or other bonding site formed by the ligand. Examples of ligands include crown ethers such as 12-crown-4, 15-crown-5, 18-crown-6, and 4,13-diaza-18-crown-6, polycyclic ligands such as 4,7,13,16,21-pentaoxa-1,10-diaza bicyclo [8,8,5] heneicosane, and monovalent or polyvalent forms thereof. Other examples of ligands include cryptand structures such as those described with Formulas II and III below. In one embodiment, a light emissive group includes one or more ligands and one or more luminescers.

The word "monolayer" and "layer" are used interchangeably herein to designate a layer of molecules or atoms is present on the surface, not to indicate that a perfect monolayer of molecules or atoms is formed, i.e., there is one molecule or atom present in every available position on the surface. There may be gaps or defects present in a layer of molecules or atoms present on the surface, as long as the gaps or defects do not prevent the desired function.

The term "conductive layer" refers to a structure formed from one or more electrically conductive materials. Examples of electrically conductive materials include metals, such as copper, silver, gold, platinum, palladium, and aluminum; metal oxides, such as platinum oxide, palladium oxide, aluminum oxide, magnesium oxide, titanium oxide, tin oxide, indium tin oxide, molybdenum oxide, tungsten oxide, and ruthenium oxide; and electrically conductive polymeric materials. For certain applications, an electrically conductive material can be deposited on or otherwise applied to a substrate to form a conductive layer. For example, an electrically conductive material can be deposited on a glass substrate or a silicon wafer or a plastic substrate to form a conductive layer. The substrate can be flexible. In other applications, the substrate is itself conductive. In some instances, a conductive layer can have a substantially uniform thickness and a substantially flat outer surface. In other instances, a conductive layer can have a variable thickness and a curved, stepped, or jagged outer surface. As used herein, "outer" means the side of the layer that is away from the substrate. A conductive layer can be configured as an anode layer or a cathode layer. For certain applications, a conductive layer can be substantially transparent or translucent. For example, a conductive layer can be formed from an electrically conductive material that is substantially transparent or translucent, such as, for example, magnesium oxide, indium tin oxide, or an electrically conductive polymeric material. As another example, a conductive layer can be formed with a thickness that allows light to be transmitted through the conductive layer.

The following examples are provided as a guide. for a practitioner of ordinary skill in the art. The examples should not be construed as limiting the invention, as the examples merely provide specific methodology useful in understanding and practicing some embodiments of the invention.

Organic Light Emitting Devices

Synthesis of various parts of the structures disclosed herein have been discussed in the literature, e.g., Dhirani et al., J.A.C.S., 118, 3319, (1996); *Supramolecular Chemistry*, Jean-Marie Lehr, Venlog Sgesellschaft, Weinhein Germany. Typical literature discussing the synthesis of various supramolecular cryptands include: Juan-Carlos Rodriguez-Ubis' et al., *Synthesis of the Sodium Cryptates of Macrobicyclic Ligands Containing Bipyridine and Phenanthroline Groups*, Helvetica Chemica Acta, Vol. 67 (1984) pp. 2264-2269; Beatrice Alpha et al., *Synthesis and Characterisation of the Sodium and Lithium Cryptates of Macrobicyclic Ligands Incorporating Pyridine, Bipyridine, and Biisoquinoline Units*, Helvetica Chemica Acta, Vol. 71 (1988), pp.1042-1052; and Krzysztof E. Krakowiak et al., *Synthesis of the Cyrptands. A Short Review*, Israel Journal of Chemistry, Vol. 32, 1992, pp. 3-13. Self assembly procedures for cryptands are discussed in D. N. Reinhoud et al., Science, 295, 5564: 2403; Blasse, Chem. Phys. Lett. 246 (1988), 347-351.

FIG. 1 illustrates a side sectional view of an organic light emitting device 100 in accordance with an embodiment of the invention. The organic light emitting device 100 can be incorporated in a display device, such as, for example, an image display device such as FIGS. 7, 8 and 10.

The organic light emitting device 110 includes a first conductive layer 102 and a second conductive layer 104. In the illustrated embodiment, the first conductive layer 102 can be configured as an anode layer, while the second conductive layer 104 can be configured as a cathode layer. Typically, at least one of the first conductive layer 102 and the second conductive layer 104 is substantially transparent or translucent. In the illustrated embodiment, the second conductive layer 104 is substantially transparent to allow emitted light to be transmitted through the second conductive layer 104.

As illustrated in FIG. 1, the organic light emitting device 110 also includes a set of pixel elements 106A, 106B, and 106C positioned between the first conductive layer 102 and the second conductive layer 104. While three pixel elements 106A, 106B, and 106C are illustrated in FIG. 1, it is contemplated that more or less pixel elements can be used depending on the specific application. The pixel elements 106A, 106B, and 106C are configured to emit light when a voltage is applied to the first conductive layer 102 and the second conductive layer 104. In particular, when a voltage is applied, the pixel elements 106A, 106B, and 106C are configured to provide transport of electrical energy between the first conductive layer 102 and the second conductive layer 104, and the pixel elements 106A, 106B, and 106C are configured to emit light in response to this transport of electrical energy. Although in FIG. 1, each pixel element is shown as comprising one light emitting molecule, there can be more than one light emitting molecule in each pixel element. Each light emitting molecule in a pixel element can be the same or different. For example, a pixel element can comprise a set of molecules that emit red, blue or green light. Alternatively, a pixel element can comprise more than one molecule that emits the same wavelength of light. Alternatively, a pixel element can comprise more than one molecule that emits different wavelengths of light.

In the illustrated embodiment, the pixel elements 106A, 106B, and 106C are arranged between the first conductive layer 102 and the second conductive layer 104. In FIG. 1, the pixel elements 106A, 106B, and 106C are arranged in a substantially ordered array, such that the pixel elements 106A, 106B, and 106C are substantially regularly spaced apart from one another. As illustrated in FIG. 1, the pixel elements 106A, 106B, and 106C are substantially aligned with respect to a common direction indicated by arrow "A". This common direction defines an angle with respect to a direction orthogonal to the first conductive layer 102, which direction is indicated by arrow "B". In general, this angle can range from about 0 to about 90 degrees, such as, for example, from about 0 to about 25 degrees or from about 0 to about 10 degrees. As illustrated in FIG. 1, arrow "A" is substantially aligned with respect to arrow "B", and, hence, the pixel elements 106A, 106B, and 106C are substantially orthogonal to the first conductive layer 102.

As illustrated in FIG. 1, the pixel element 106A includes a light emitting molecule 108A. The light emitting molecule 108A is elongated and extends between the first conductive layer 102 and the second conductive layer 104. In the illustrated embodiment, the light emitting molecule 108A includes a number of groups, including an anchoring group 110A, a charge transport group 112A, a light emissive group 116A, and a charge transfer group 118A. While four groups 110A, 112A, 116A, and 118A are illustrated in FIG. 1, it is contemplated that the light emitting molecule 108A can include more or less groups depending on the specific application, as described further herein.

The anchoring group 110A is configured to bond the light emitting molecule 108A to the first conductive layer 102. By bonding the light emitting molecule 108A to the first conductive layer 102, the anchoring group 110A can serve to maintain the spacing and alignment of the light emitting molecule 108A with respect to an adjacent light emitting molecule ("spacing" refers to the distance between light emitting molecules and "alignment" refers to the orientation of the light emitting molecules with respect to the conductive layer (arrow "A") of FIG. 1). If there is more than one light emitting molecule in a pixel, array or device, the light emitting molecules can have different alignments and spacings. Also, the anchoring group 110A serves to facilitate transport of electrical energy between the first conductive layer 102 and the charge transport group 112A.

In the illustrated embodiment, the anchoring group 110A is configured to form a chemical bond with the first conductive layer 102. In particular, the anchoring group 110A can include an atom, such as, for example, a nitrogen atom, an oxygen atom, a silicon atom, or a sulfur atom, and this atom can be configured to form a chemical bond with the first conductive layer 102. The chemical bond can be, for example, a covalent bond, a chemisorptive bond, or a combination thereof. Examples of anchoring groups include carboxy groups, thio groups, disulfide groups, amino groups, alkylamino groups, silyl groups, and siloxy groups. In some instances, one or more atoms of the anchoring group 110A can be removed to allow bonding to the first conductive layer 102. For example, a hydrogen atom of a thio group can be removed to allow formation of a chemical bond between a sulfur atom of the thio group and the first conductive layer 102. As another example, a proton of a carboxy group can be removed to allow formation of one or more chemical bonds between oxygen atoms of the carboxy group and the first conductive layer 102.

Typically, selection of the anchoring group 110A will depend on its ability to form a chemical bond with the first conductive layer 102. For example, when the first conductive layer 102 is formed from a metal oxide such as indium tin oxide, the anchoring group 110A desirably includes an oxygen atom or a silicon atom to allow formation of a chemical bond between the oxygen atom or the silicon atom and the metal oxide. As another example, when the first conductive layer 102 is formed from a metal such as gold, the anchoring group 110A desirably includes a sulfur atom to allow formation of a chemical bond between the sulfur atom and the metal.

In some instances, the anchoring group 110A can include an atom that is configured to form multiple chemical bonds with the first conductive layer 102. For example, the anchoring group 110A can include a silicon atom that can form up to 3 chemical bonds with the first conductive layer 102. In other instances, the anchoring group 110A can include multiple atoms that can each form a chemical bond with the first conductive layer 102, which multiple atoms can be the same or different. For example, the anchoring group 110A can include multiple oxygen atoms or multiple sulfur atoms that can each form a chemical bond with the first conductive layer 102.

As illustrated in FIG. 1, the charge transport group 112A has a first end 120A, a second end 122A, and a longitudinal axis 114A. The first end 120A of the charge transport group 112A is bonded to the anchoring group 110A. In the illustrated embodiment, the first end 120A of the charge transport group 112A is configured to form a covalent bond with the anchoring group 110A.

The charge transport group 112A is configured to provide transport of electrical energy between the anchoring group 110A and the light emissive group 116A. In the illustrated embodiment, the transport of electrical energy is substantially one-dimensional. In particular, the transport of electrical energy can occur substantially along the longitudinal axis 114A of the charge transport group 112A. In the example illustrated in FIG. 1, the longitudinal axis 114A of the charge transport group 112A is substantially aligned with respect to arrow "A" and arrow "B", and, hence, the transport of electrical energy is substantially orthogonal to the first conductive layer 102.

Typically, selection of the charge transport group 112A will depend on a number of desired characteristics. For example, selection of the charge transport group 112A can depend on an electrical conductivity of the charge transport group 112A. The electrical conductivity is measured by methods based on the level of conjugation known in the art, such as those described in Collier, Science 285, 391 (1999) or Davis, Nature 396, 60-63 (1998), for example. Also, selection of the charge transport group 112A can depend on a solubility imparted by the charge transport group 112A during formation of the organic light emitting device 110 or a spacing or alignment of the light emitting molecule 108A with respect to an adjacent light emitting molecule.

In some instances, the charge transport group 112A is a conjugated group that comprises a set of conjugated π-bonds. Advantageously, the set of conjugated π-bonds serves to facilitate transport of electrical energy between the anchoring group 110A and the light emissive group 116A. Examples of groups that can be used to form a conjugated group include alkylene groups, alkenylene groups, alkynylene groups, arylene groups, and iminylene groups.

For example, in one embodiment, charge transport group 112A comprises a conjugated group having a single arylene group or single aromatic group or combination thereof. In one embodiment, charge transport group is given by formula (-A-B)$_m$-A, where A is an arylene group, and B is an alkenylene group, an alkynylene group, or an iminylene group. Here, m is an integer that can be, for example, in the range of 1 to 19. In this example, the conjugated group includes m+1 arylene groups, and the m+1 arylene groups are bonded to one another to form a chain structure. For certain applications, the conjugated group desirably includes 3 to 4 arylene groups. Each successive pair of arylene groups of the chain structure is bonded to one another via an alkenylene group, an alkynylene group, or an iminylene group. Advantageously, the chain structure can be substantially linear and can define the longitudinal axis 114A.

In some instances, a conjugated group can be formed from one or more branched or substituted groups to provide a desired spacing or alignment of the light emitting molecule 108A with respect to an adjacent light emitting molecule. For example, a substitution group such as an alkyl group can serve to increase spacing of the light emitting molecule 108A with respect to an adjacent light emitting molecule. Such increased spacing can be desirable to prevent or reduce electrical coupling between the light emitting molecule 108A and an adjacent light emitting molecule. It is also contemplated that a conjugated group can be formed from one or more branched or substituted groups to provide a desired level of solubility during formation of the organic light emitting device 100. It is further contemplated that a conjugated group can be formed from one or more branched or substituted groups to provide a desired level of electrical conductivity of the light emitting molecule 108A. For example, a substitution group such as an electron accepting group or an electron donating group can affect density of charged species along the conjugated group and can be selected to provide the desired level of electrical conductivity. In some instances, an electron donating group can increase density of charged species along the conjugated group and can serve to increase electrical conductivity of the conjugated group.

As illustrated in FIG. 1, the light emissive group 116A is bonded to the second end 122A of the charge transport group 112A. In the illustrated embodiment, the light emissive group 116A is configured to form a covalent bond with the second end 122A of the charge transport group 112A.

The light emissive group 116A is configured to emit light in response to transport of electrical energy by the charge transport group 112A. In the illustrated embodiment, the light emissive group 116A is configured to emit light having a particular wavelength or range of wavelengths. In particular, the light emissive group 116A can include a luminescer, and the luminescer can be configured to emit light having a particular wavelength or range of wavelengths.

Typically, selection of the light emissive group 116A will depend on a particular wavelength or range of wavelengths of light that is emitted. For example, when the organic light emitting device 110 is incorporated in a display device, the light emissive group 116A desirably includes a luminescer that is configured to emit light that is detectable in the visible wavelength range. In particular, the luminescer can be a lanthanide metal ion that is configured to emit light in the range of 410 nm to 650 nm. For example, $Eu^{3+}$, $Dy^{3+}$, and $Tb^{3+}$ are typically configured to emit light having a red color, a blue color, and a green color, respectively. The use of lanthanide metal ions to emit light is known in the art.

In some instances, the light emissive group 116A can include a ligand that is configured to bond to a luminescer. In particular, the ligand can bond to the luminescer to form a ligand-luminescer complex. The ligand can include a set of coordination atoms configured to form coordination bonds with the luminescer. In some instances, the ligand can encage the luminescer within a cavity or other bonding site formed by the ligand. By encaging the luminescer, the ligand can serve to protect the luminescer from deactivating conditions during formation of the organic light emitting device 110 or during end use. Also, the ligand can facilitate emission of light by the luminescer via an absorption-energy transfer-emission mechanism.

As illustrated in FIG. 1, the charge transfer group 118A is bonded to the light emissive group 116A. In the illustrated embodiment, the charge transfer group 118A is configured to form a covalent bond with the light emissive group 116A.

In addition, the charge transfer group 118A is configured to bond the light emitting molecule 108A to the second conductive layer 104. By bonding the light emitting molecule 108A to the second conductive layer 104, the charge transfer group 118A serves to maintain the spacing and alignment of the light emitting molecule 108A with respect to an adjacent light emitting molecule. Also, the charge transfer group 118A serves to facilitate transport of electrical energy between the second conductive layer 104 and the light emissive group 116A.

In some instances, the charge transfer group 118A can have a configuration that is similar to that of the anchoring group 110A. Thus, for example, the charge transfer group 118A can include an atom that is configured to form a chemical bond with the second conductive layer 104. The chemical bond can be, for example, a covalent bond, a chemisorptive bond, or a combination thereof. In other instances, the charge transfer group 118A can be configured to bond the light emitting molecule 108A to the second conductive layer 104 using a number of other mechanisms. For example, the charge transfer group 118A can be bonded to the second conductive layer 104 via any mechanical, physical, or electrical coupling that is adequate to facilitate transport of electrical energy between the second conductive layer 104 and the light emissive group 116A.

In the illustrated embodiment, the pixel elements 106B and 106C have configurations that are similar to that of the pixel element 106A. Thus, as illustrated in FIG. 1, the pixel element 106B includes a light emitting molecule 108B that is elongated and extends between the first conductive layer 102 and the second conductive layer 104. The light emitting molecule 108B includes an anchoring group 110B, a charge transport group 112B, a light emissive group 116 B, and a charge transfer group 118B. The charge transport group 112B has a first end 120B, a second end 122B, and a longitudinal axis 114B. Similarly, the pixel element 106C includes a light emitting molecule 108C that is elongated and extends between the first conductive layer 102 and the second conductive layer 104. The light emitting molecule 108C includes an anchoring group 110C, a charge transport group 112C, a light emissive group 116C, and a charge transfer group 118C. The charge transport group 112C has a first end 120C, a second end 122C, and a longitudinal axis 114C.

The configuration of the organic light emitting device 110 can offer a number of advantages, such as, for example, improved transport of electrical energy, improved robustness and thermal stability, improved visual characteristics, reduced energy requirements, and reduced weight. In the illustrated embodiment, the pixel elements 106A, 106B, and 106C are formed as a monolayer of the light emitting molecules 108A, 108B, and 108C, and the light emitting molecules 108A, 108B, and 108C are arranged in a substantially ordered array. When a voltage is applied to the first conductive layer 102 and the second conductive layer 104, the light emitting molecules 108A, 108B, and 108C can provide transport of electrical energy substantially along the common direction indicated by arrow "A". In particular, the light emitting molecules 108A, 108B, and 108C can provide substantially one-dimensional electrical pathways for charged species (e.g., electrons) as they travel from the first conductive layer 102 to the second conductive layer 104.

Figure 2:
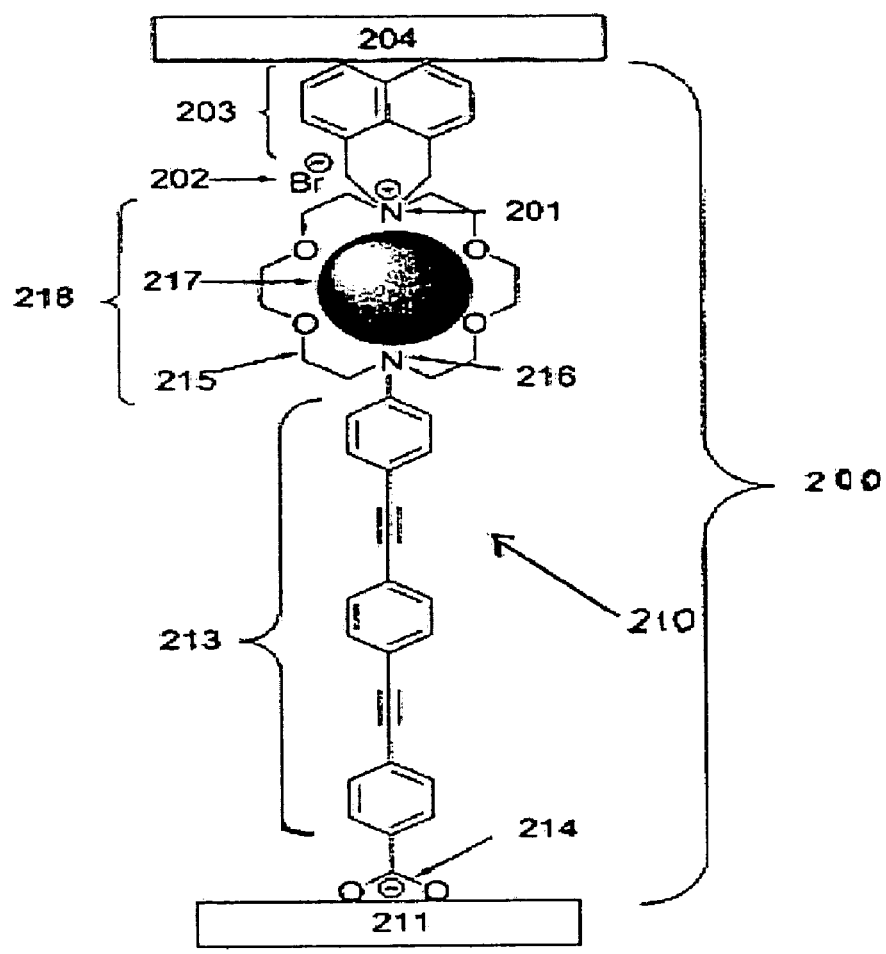
FIG. 2 illustrates a pixel element according to an embodiment of the invention.

Attention next turns to FIG. 2, which illustrates a pixel element 200 in accordance with an embodiment of the invention. As illustrated in FIG. 2, the pixel element 200 includes a light emitting molecule 210. The light emitting molecule 210 is elongated and extends between a first conductive layer 211 and a second conductive layer 204. In the illustrated embodiment, the light emitting molecule 210 includes a number of groups, including an anchoring group 214, a charge transport group 213, a light emissive group 218, and a charge transfer group 203.

The anchoring group 214 is bonded to the first conductive layer 211, which can be configured as an anode layer. When a voltage is applied to the first conductive layer 211 and the second conductive layer 204, the anchoring group 214 can facilitate transport of charged species from the first conductive layer 211 to the charge transfer group 213.

In the illustrated embodiment, the anchoring group 214 is a negatively charged carboxy group. In particular, a proton of the carboxy group is removed to allow formation of two chemical bonds between oxygen atoms of the carboxy group and the first conductive layer 211. As illustrated in FIG. 2, bonding of the two oxygen atoms to the first conductive layer 211 is substantially symmetrical, such that the light emitting molecule 210 is substantially orthogonal to the first conductive layer 211. However, depending on the characteristics of the first conductive layer 211, bonding of the two oxygen atoms to the first conductive layer 211 can be asymmetrical, such that the light emitting molecule 210 can be tilted at an angle with respect to a direction orthogonal to the first conductive layer 211.

The charge transport group 213 is bonded to the anchoring group 214 and extends upwardly from the anchoring group 214. When a voltage is applied to the first conductive layer 211 and the second conductive layer 204, the charge transport group 213 can facilitate transport of charged species from the anchoring group 214 to the light emissive group 218. In particular, the charge transport group 213 can serve to provide a substantially one-dimensional electrical pathway for the charged species as they travel from the anchoring group 214 to the light emissive group 218.

In the illustrated embodiment, the charge transport group 213 is a triphenylene diethynylene. Advantageously, the triphenylenediethynylene includes a set of conjugated π-bonds that substantially extend through a length of the triphenylenediethynylene. The triphenylenediethynylene includes three phenylenes bonded to one another to form a chain structure, and each successive pair of phenylenes of the chain structure is bonded to one another via an ethynylene. The phenylenes can serve as stiffeners to maintain the spacing and alignment of the light emitting molecule 210 with respect to an adjacent light emitting molecule. The ethynylenes can serve to reduce or prevent steric interference between hydrogen atoms of adjacent phenylenes. Accordingly, the ethynylenes can serve to reduce or prevent distortions that can lead to the formation of non-conjugated portions. While three phenylenes and two ethynylenes are illustrated in FIG. 2, it is contemplated that the charge transport group 213 can include more or less groups depending on the specific application. Also, while the triphenylenediethynylene illustrated in FIG. 2 includes phenylenes that are bonded to ethynylenes in a para configuration, it is contemplated that one or more phenylenes can be bonded to ethynylenes in other configurations, such as, for example, an ortho configuration or a meta configuration.

As illustrated in FIG. 2, the light emissive group 218 is bonded to the charge transport group 213 via a nitrogen atom 216. When a voltage is applied to the first conductive layer 211 and the second conductive layer 204, the light emissive group 218 can emit light in response to transport of charged species towards the light emissive group 218.

In the illustrated embodiment, the light emissive group 218 includes a lanthanide metal ion 217, namely $Eu^{3+}$. $Eu^{3+}$ is typically configured to emit light having a red color. As illustrated in FIG. 2, the light emissive group 218 also includes a ligand 215 that bonds to the $Eu^{3+}$ to form a ligand-$Eu^{3+}$ complex. In the illustrated embodiment, the ligand 215 is a positively charged, trivalent form of a 4,13-diaza-18-crown-6. Advantageously, the ligand 215 encages the $Eu^{3+}$ within a cavity formed by the ligand 215. By encaging the $Eu^{3+}$, the ligand 215 can protect the $Eu^{3+}$ from deactivating conditions during formation of the pixel element 200 or during end use. Also, the ligand 215 can facilitate emission of light by the $Eu^{3+}$ via an absorption-energy transfer-emission mechanism. In particular, transport of charged species by the charge transport group 213 can cause emission of light outside the visible range. In particular, one or more phenylene groups forming the charge transport group 213 can emit light in the ultraviolet range in response to the transport of charged species. The ligand 215 can absorb emitted light in the ultraviolet range and can transfer energy to the $Eu^{3+}$, which can then emit light having a red color.

The charge transfer group 203 is bonded to the light emissive group 218 via a positively charged nitrogen atom 201. As illustrated in FIG. 2, a negatively charged bromine atom 202 is positioned adjacent to the positively charged nitrogen atom 201 and can serve as a counter ion. The charge transfer group 203 is also bonded to the second conductive layer 204, which can be configured as a cathode layer. When a voltage is applied to the first conductive layer 211 and the second conductive layer 204, the charge transfer group 203 can facilitate transport of charged species from the light emissive group 218 to the second conductive layer 204. In the illustrated embodiment, the positively charged nitrogen atom 201 can serve as an electron accepting group and can facilitate transport of charged species towards the second conductive layer 204.

In the illustrated embodiment, the charge transfer group 203 is a bivalent form of a 1,8-dimethylnaphthalene. Advantageously, the charge transfer group 203 can facilitate emission of light by the $Eu^{3+}$ via an absorption-energy transfer-emission mechanism. As discussed previously, transport of charged species by the charge transport group 213 can cause emission of light outside the visible range. The charge transfer group 203 can absorb emitted light in the ultraviolet range and can transfer energy to the $Eu^{3+}$, which can then emit light having a red color.

Figure 3:
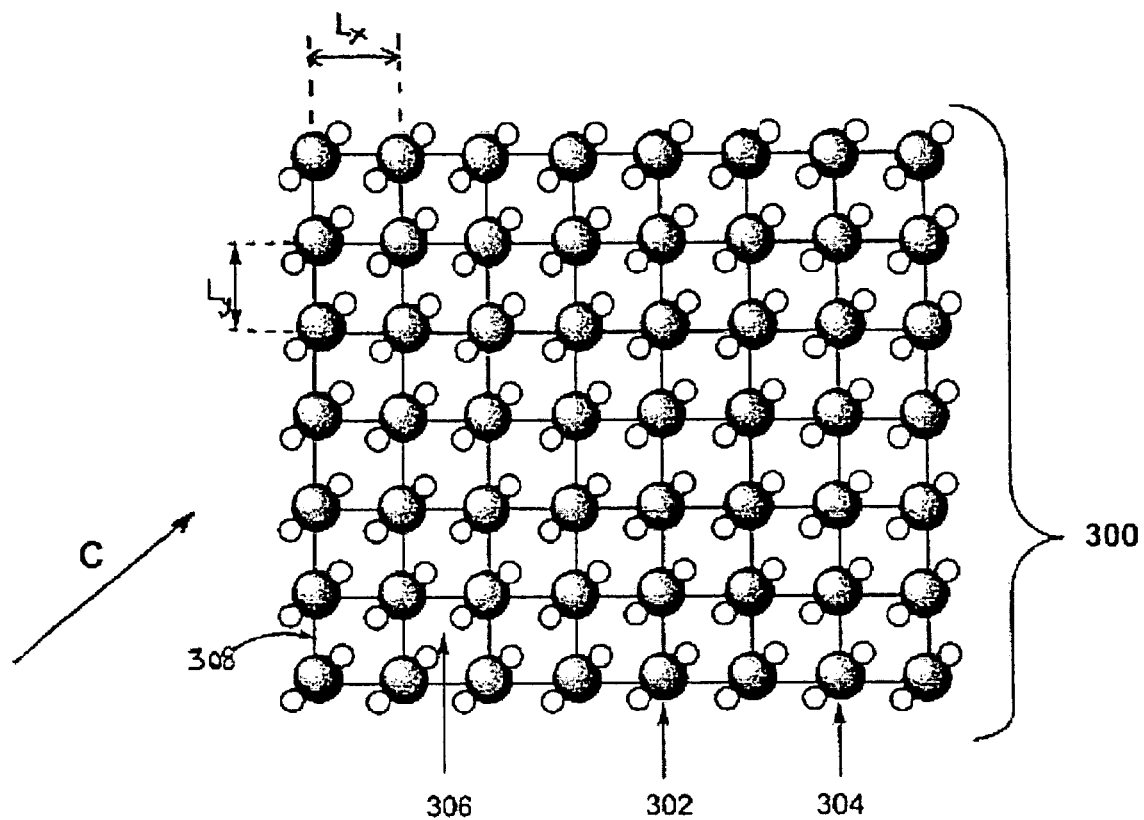
FIG. 3 illustrates a top sectional view of an organic light emitting device according to an embodiment of the invention.

FIG. 3 illustrates a top sectional view of an organic light emitting device 300 in accordance with an embodiment of the invention. In particular, FIG. 3 illustrates various anchoring groups (e.g., anchoring groups 302 and 304) of a set of pixel elements. The anchoring groups are positioned on a surface 306 of a conductive layer 308, which can be configured as an anode layer.

In the illustrated embodiment, the anchoring groups are carboxy groups.

Each carboxy group includes a carbon atom (shown shaded in FIG. 3) and a pair of oxygen atoms (shown unshaded in FIG. 3). Protons of the carboxy groups can be removed to allow formation of chemical bonds between oxygen atoms of the carboxy groups and the conductive layer 308.

As illustrated in FIG. 3, the anchoring groups are arranged in an array on the surface 306 of the conductive layer 308. In particular, the anchoring groups are arranged in a substantially ordered array, such that the anchoring groups are substantially regularly spaced apart from one another. As illustrated in FIG. 3, the carbon atoms of the anchoring groups are substantially positioned at intersection points of an imaginary rectangular lattice, and the oxygen atoms of the anchoring groups are substantially aligned with respect to a common direction indicated by arrow "C". The rectangular lattice can be characterized by lattice spacings $L_x$ and $L_y$, which can be the same or different. In the illustrated embodiment, the lattice spacings $L_x$ and $L_y$ can each be in the range of about 0.1 nm to about 10 nm, such as, for example, from about 0.1 nm to about 1 nm.

Depending on the particular application, the spacing and alignment of the anchoring groups can be varied from that illustrated in FIG. 3. For example, it is contemplated that the anchoring groups can be positioned at intersection points of various other types of 2-dimensional lattices, such as hexagonal lattices and centered lattices. As another example, it is contemplated that the anchoring groups can be randomly positioned on the surface 306 or can be concentrated in one or more portions of the surface 306. As a further example, it is contemplated that the anchoring groups can be randomly aligned or can be aligned with respect to two or more different directions.

Examples of Light Emitting Molecules

One embodiment of light emitting molecules of the invention is illustrated by formula (I):

(I)

where R1 is an anchoring group; R2 is a charge transport group; R3 is a pre-light emissive group capable of bonding to a luminescer; R4 is a charge transfer group and t is an integer from 1 to 19;

R1 is preferably selected from the group consisting of: silanes, organic acids, amines, thiols, disulfide, amino, and alkylamino.

In one particular class of light emitting molecules, pre-light emissive group R3 is given by formula (II):

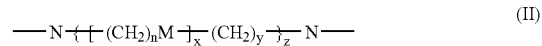
(II)

where M is independently selected from the group consisting of: O, NH, NR and S, where R is a small alkyl group and the N's may be charged; n and y are independently integers from 1 to 19; x is an integer from 1 to 19; and z is an integer from 1 to 3. In one preferred class of compounds, n and y are independently integers from 1 to 5. One particular example of compounds of formula (II) is given by the following structure:

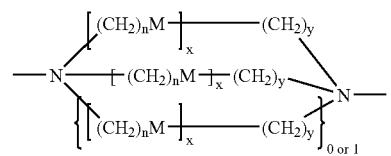

In the class of compound where R3 is given by formula (II), formula I is given by:

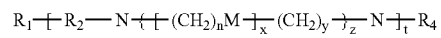

where the variables are as defined above. In a particular class of light emitting molecules, n and y are both 2; M is O; z is 2 or 3; t is 1 or 2; and x is 2.

Figure 13:
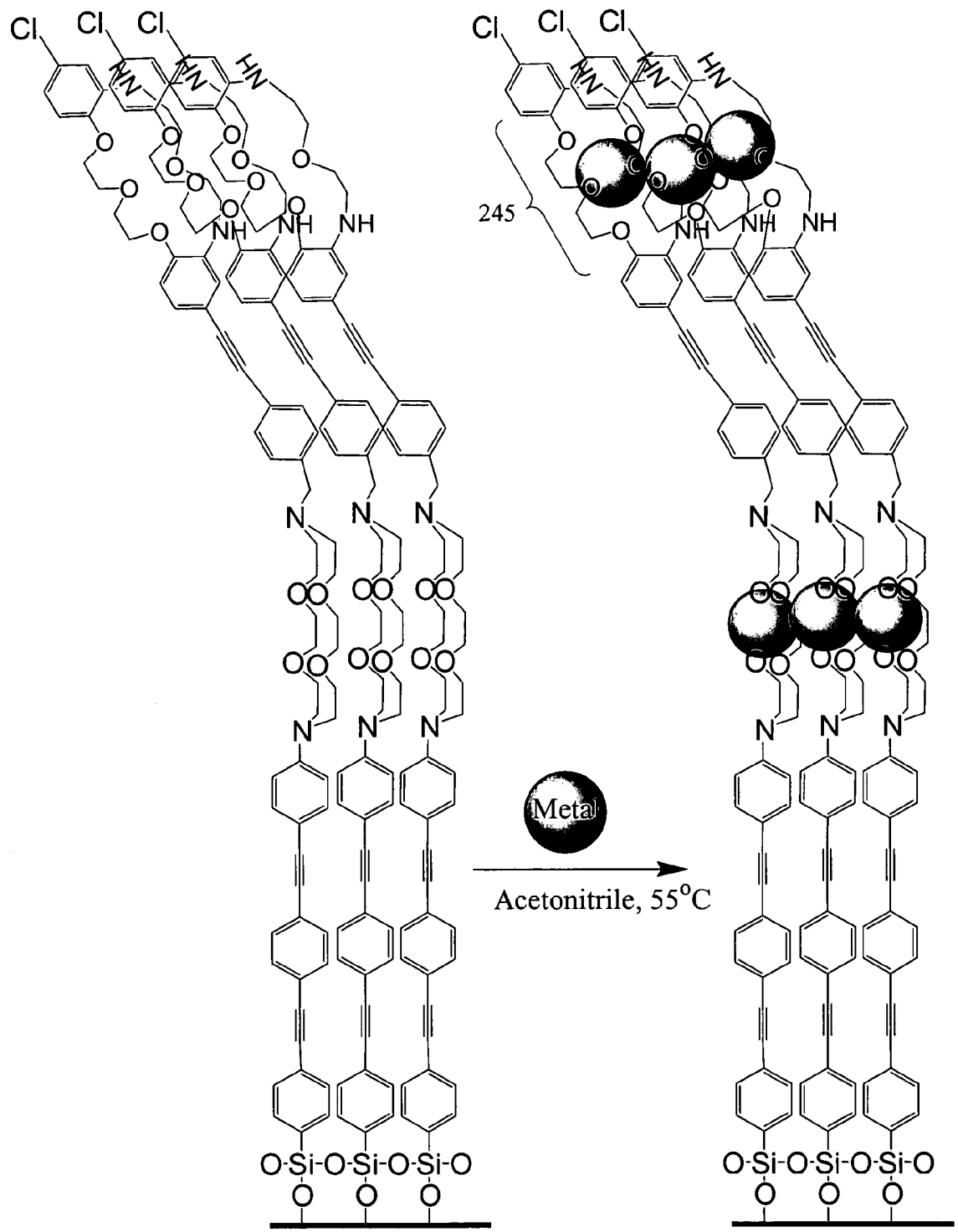
FIG. 13 illustrates one example of metal coordinating with the stacked light emitting molecule of FIG. 12.

In another class of light emitting molecules, pre-light emissive group R3 is given by formula (III):

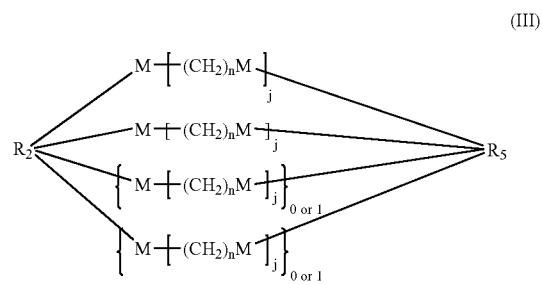
(III)

where R2 is a charge transport group; R5 is either R2 or R4; the M's are independently selected from the group consisting of: O, NH, NR and S, where R is a small alkyl group and the N's may be charged; n is an integer from 1 to 3; j is an integer from 2-5. In formula II, the light emissive group is attached to the charge transport group on one end (the R2 end) and either another charge transport group or a charge transfer group at the other end (the R5 end). The R2 and R5 groups have 2 to 4 available bonds such as phenyl rings. This type of light emissive group is shown in FIG. 13 as element 245, for example.

One example of the light emissive group of Formula (III) is shown below that illustrates the bonding of the pre-light emissive group to R2 and R5:

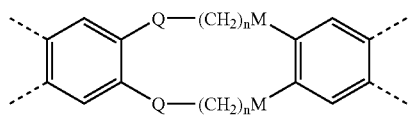

where Q is NH or O, the other variables are as defined above, and the dashed lines indicate various groups may be added onto the R2 and R5 groups, as described further herein.

In the structures above, there may be optional alkyl linkers between the groups linking the light emissive group and the remainder of the structure.

Some classes of "pre" light emissive groups include the structures shown in Scheme A:

Scheme A

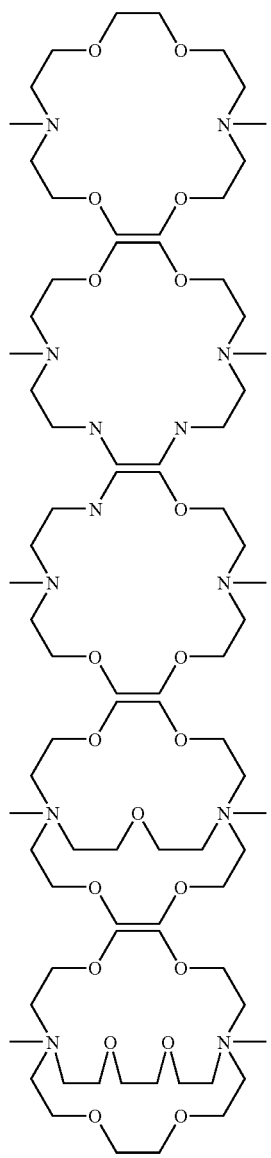

-continued

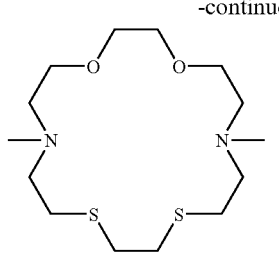

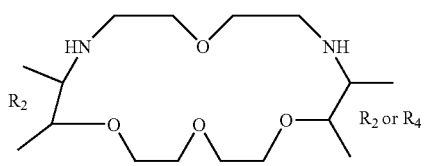

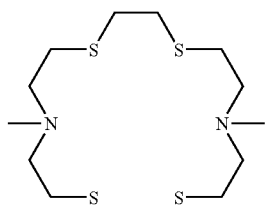

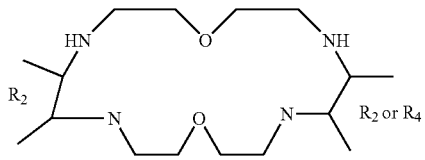

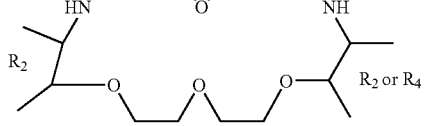

In one aspect of the use of light emitting molecules, light emitting molecules containing one or more pre-light emissive groups are coordinated to one or more luminescers, electrical energy or light energy is applied to the light emitting molecules, and the light emitting molecules emit the desired light.

Charge transport group R2 can be any conjugated group. In particular classes of compounds of the invention, charge transport group R2 is given by the structures in Scheme B. In Scheme B, w is an integer from 1 to 20 and w is preferably less than 10. In a class of charge transport groups of the invention, w is an integer from 1 to 5. In another class of charge transport groups of the invention, w is an integer from 5 to 10. If there is more than one w in a structure, the w's may be the same or different. In another class of charge transport groups of the invention, w is an integer from 1 to 10. In another class of charge transport groups of the invention, w is an integer from 2 to 5. It is understood that any of the components of the charge transport groups shown in Scheme B and given herein may be repeated and combined in any order, as long as the resulting structure has the functions of the charge transport group described herein.

Scheme B

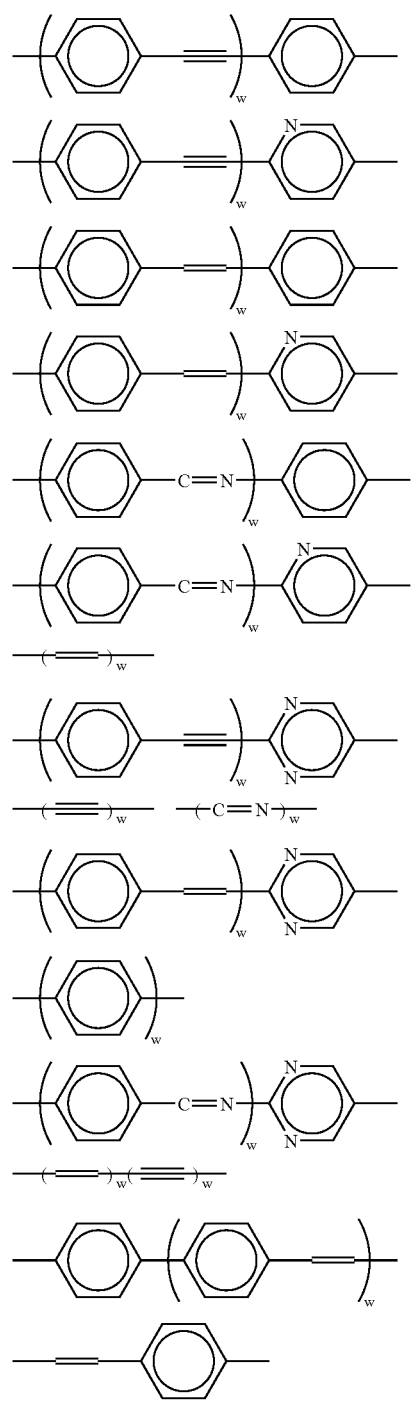

-continued

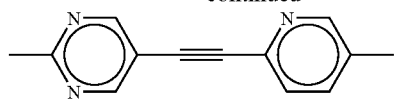
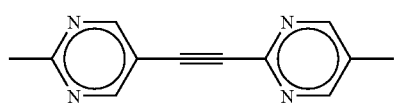
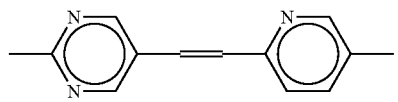
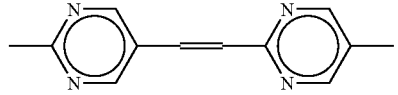
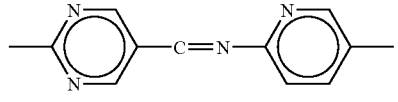
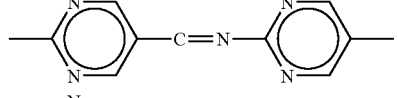
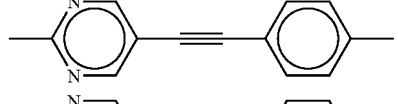
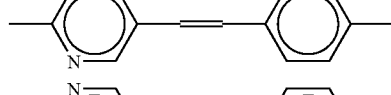
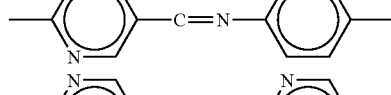
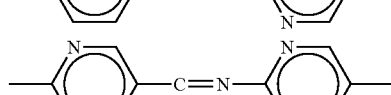
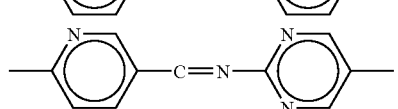
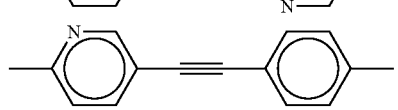

-continued

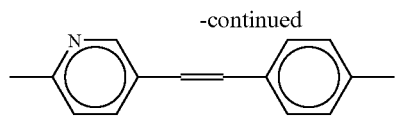

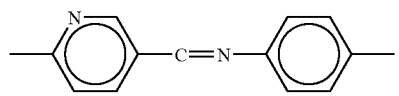

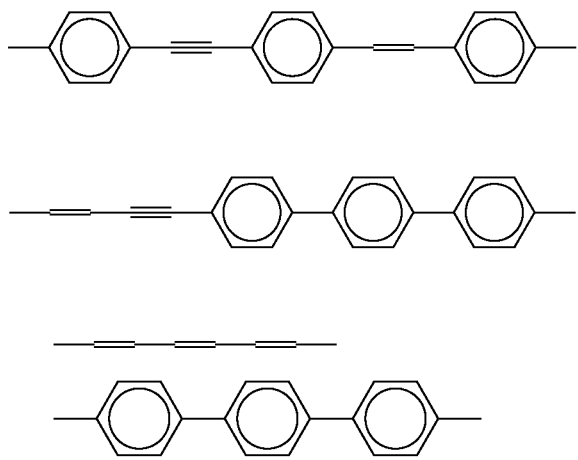

In particular classes of compounds of the invention, charge transport group R3 is given by the formula:

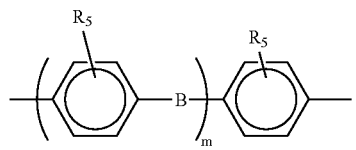

where m is an integer from 1 to 19 and B is an alkenylene, alkynylene or imidylene group. There are optionally one or two substituents R5 in the ring structures. R5 is independently an electron donating group; an electron withdrawing group; a halogen; —OH; or —OR, where R is a small alkyl group. One or two of the ring carbons of any ring may be replaced with a nitrogen.

In particular classes of compounds of the invention, R4 may be the same as described for the charge transport group. In other particular classes of compounds of the invention, R4 is independently selected from the group consisting of: hydrogen, alkyl groups, alkylene groups, alkenyl groups, alkenylene groups, alkynyl groups, alkynylene groups, aryl groups, arylene groups, iminyl groups, iminylene groups, hydride groups, halo groups, hydroxy groups, alkoxy groups, carboxy groups, thio groups, alkylthio groups, disulfide groups, cyano groups, nitro groups, amino groups, alkylamino groups, dialkylamino groups, silyl groups, and siloxy groups. In one embodiment, R4 is an electron withdrawing group.

Synthesis of various components of light emitting molecules is known to one of ordinary skill in the art using the methods and description provided herein.

One particular example of light emitting molecules of formula I is given in Scheme C, which also shows the formation of a layer of light emitting molecules on a surface. In one class of light emitting molecules where R1 is a silane, multiple light emitting molecules can be linked together as shown Scheme C. Although Scheme C shows all anchoring groups linked together, it is known in the art that some anchoring groups may not be linked to other anchoring groups.

Scheme C

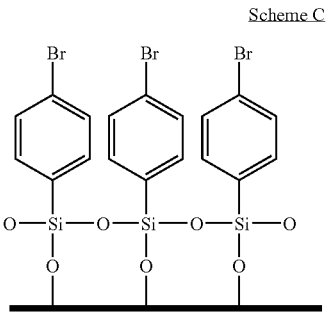

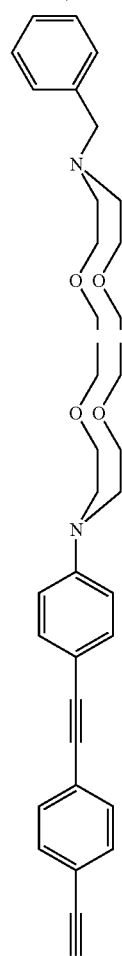

-continued

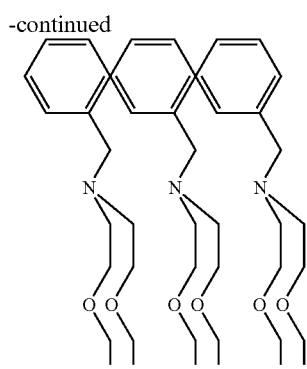

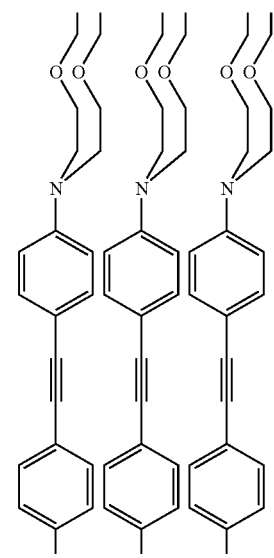

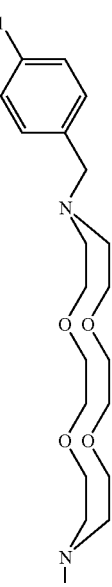

Figure 9:
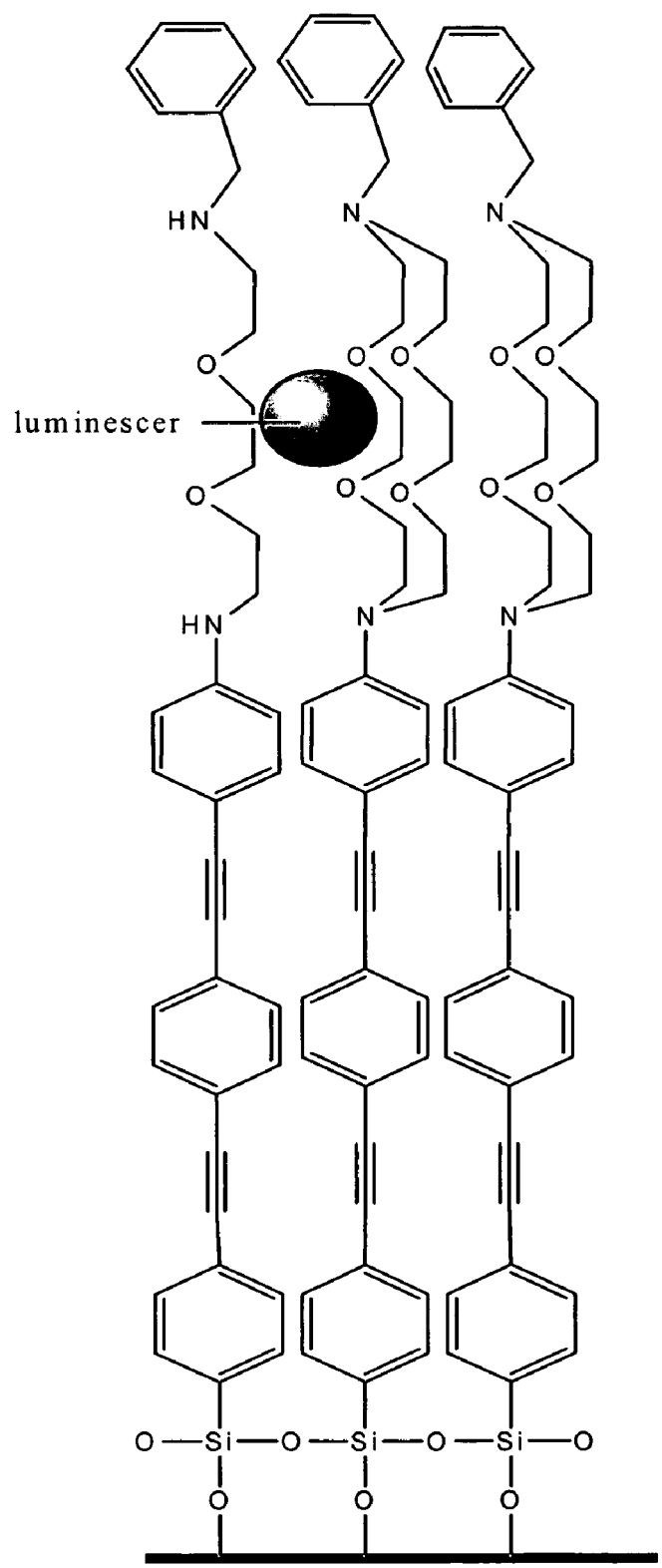
FIG. 9 illustrates one example of a light emitting molecule having a luminescer between light emissive groups.
Figure 14:
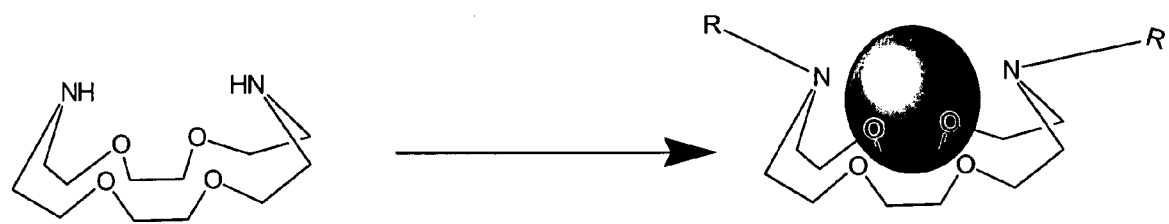
FIG. 14 shows a metal coordinating with a light emissive group.

Included herein are pre-light emitting molecules, wherein the molecule is ready to receive a luminescer. Examples of pre-light emitting molecules are given in Schemes C-E. In Schemes C-E, the pre-light emissive group is ready to receive a luminescer, such as $Eu^{3+}$. It is noted that the luminescer may not be encaged in the light-emissive group (shown in FIG. 14), but may be encaged between pre-light emissive groups (shown in FIG. 9). In particular embodiments, some luminescers may be encaged in the pre-light emissive groups and some luminescers may be positioned between the pre-light emissive groups.

Scheme D

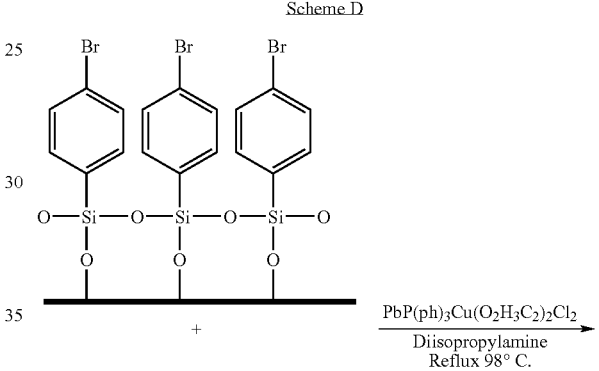

$$\xrightarrow{\substack{PbP(ph)_3Cu(O_2H_3C_2)_2Cl_2 \\ \text{Diisopropylamine} \\ \text{Reflux 98°C.}}}$$

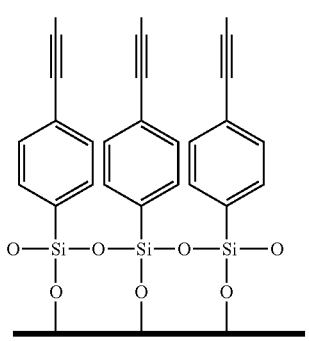

-continued

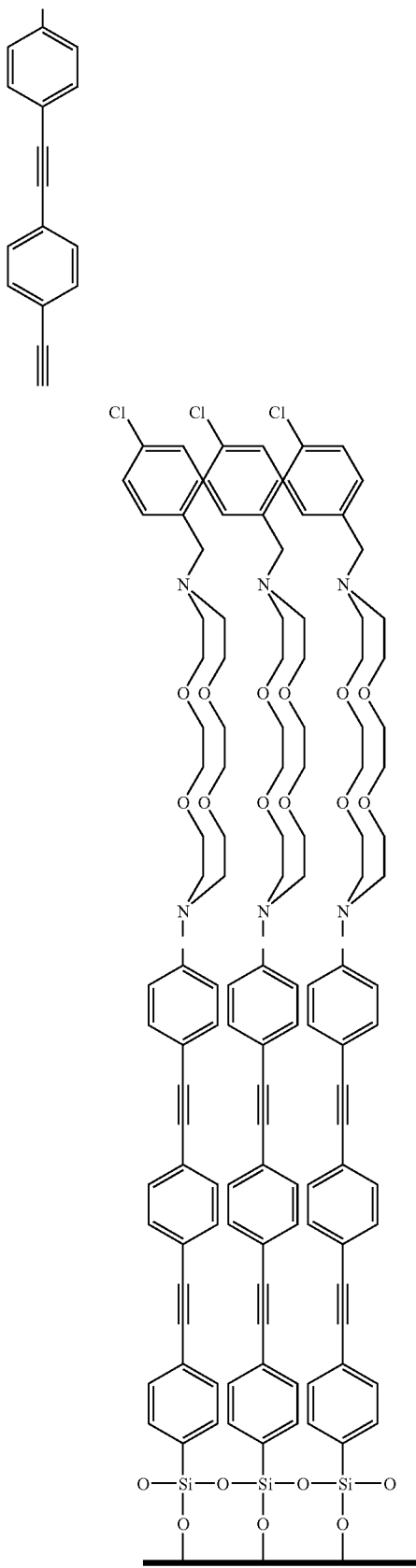

Figure 11:
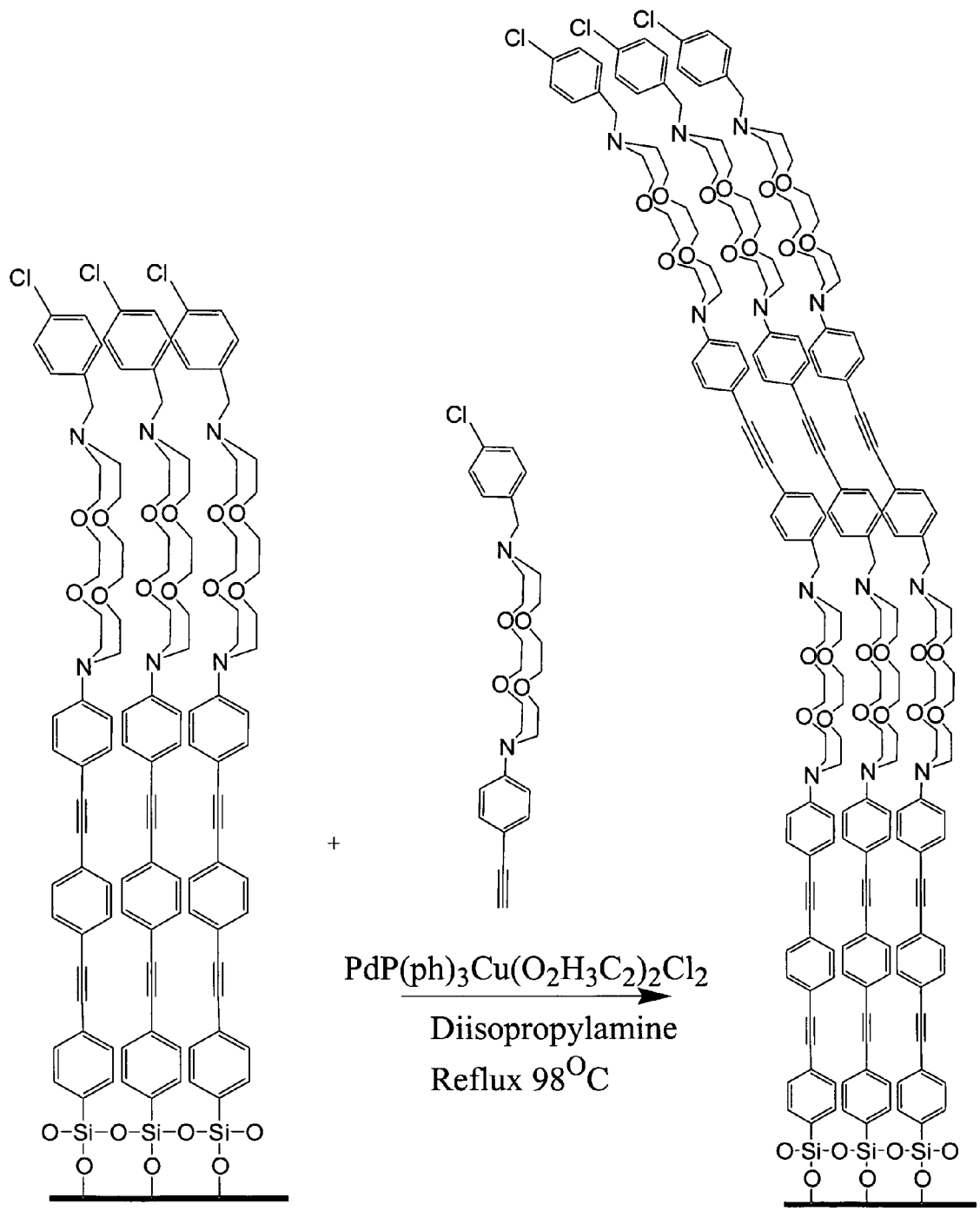
FIG. 11 and FIG. 12 illustrate examples of stacked light emitting molecules.
Figure 12:
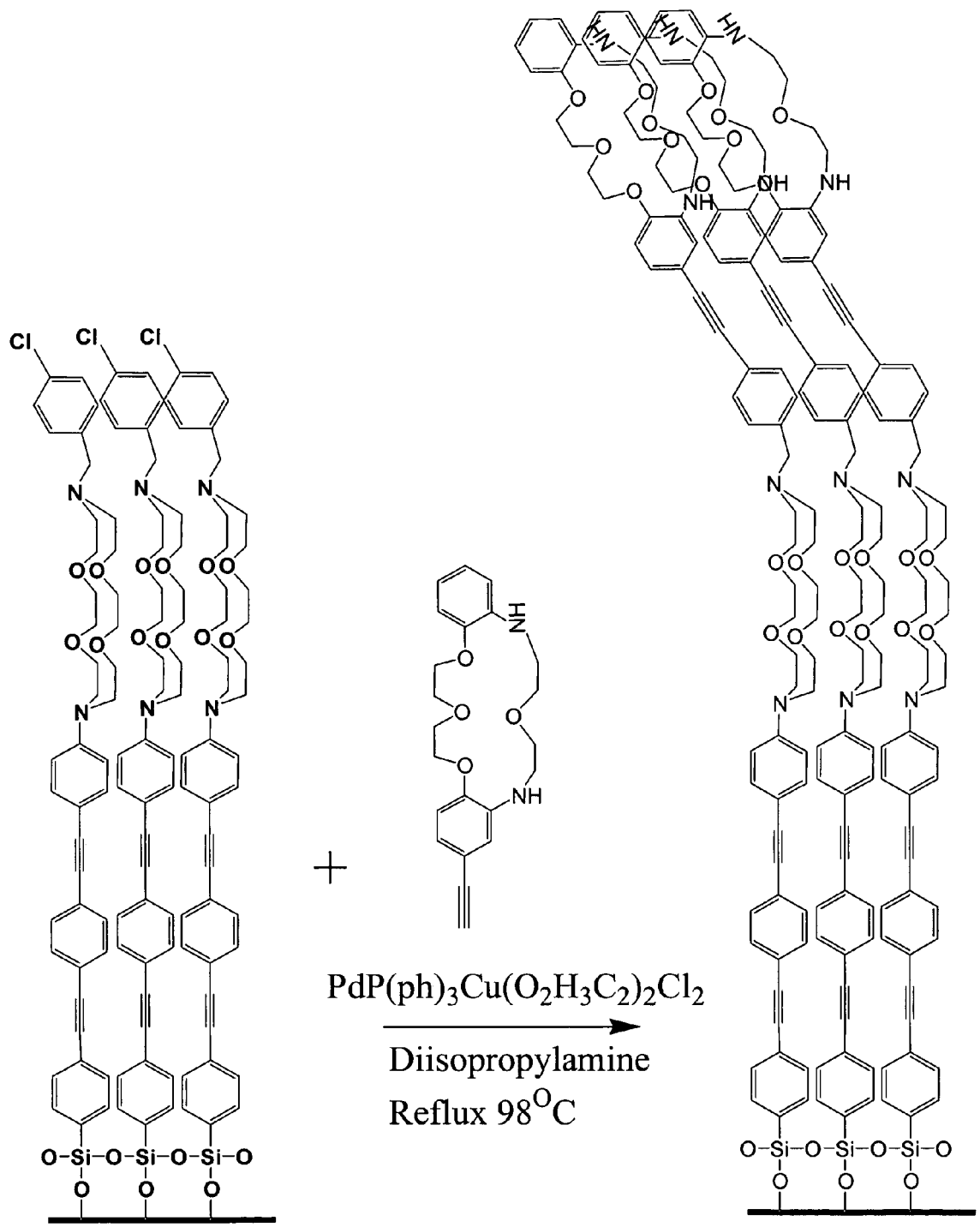

If necessary or desired to provide the desired intensity of emission, there may be more than one charge transport group and light emissive group in a given light emitting molecule. The synthesis of these stacked light emitting molecules follows the synthesis of light emitting molecules and components of light emitting molecules described herein. FIGS. 11, 12 and 13 show examples of stacked light emitting molecules. It should be noted that the charge transport groups and light emissive groups may be the same or different in stacked light emitting molecules. FIG. 13 illustrates metal coordinating with the light emissive groups in a stacked light emitting molecule. The metal can be any metal that coordinates with the light emissive groups. The metals in stacked light emitting molecules may be the same or different in a given light emitting molecule, and metals in different light emitting molecule may be the same or different.

The synthesis of the light emitting molecules described herein do not necessarily follow the pattern of bonding an anchoring group to a charge transfer group, and then bonding the resulting structure to a light emissive group, and then bonding the resulting structure to a charge transport group. For example, when the anchoring group is added to the charge transport group during formation of the charge transport group, part of the anchoring group may already include a portion of the group that will be the charge transport group in the overall structure. This is shown in Scheme D, where the first aromatic ring of the charge transport group is formed on the anchoring silane group before addition of the remainder of the molecule. Scheme E also shows synthesis of part of a light emitting molecule, where the light emissive group is formed with part of the charge transfer group and the charge transport group. Alternatively, the entire light emitting molecule may be synthesized, and then self-assembled onto a substrate. Alternatively, all parts of the light emitting molecule with the exception of the anchoring group may be synthesized, and then self-assembled onto a substrate having the anchoring group attached. The invention includes all subparts of light emitting molecules.

The light emitting molecules of this invention can be prepared by various general synthetic procedures. The molecules can for example be synthesized in a step wise fashion on a surface, the molecules can be synthesized completely and thereafter bonded to a surface, or portions of the molecules may be bonded to the surface and the remaining portions synthesized separately and then bonded to the portion that is bonded to the surface. In general, any of such molecular construction schemes can be employed to generate the surfaces having one or more light emitting molecules bonded thereto. Further, the light emitting molecules can be synthesized by complexing or otherwise bonding light emissive species, e.g., a luminescer, to pre-light emissive molecules, for example by complexing or bonding a metal atom luminescer to a ligand or coordination site within a pre-light emissive molecule. The luminescer can be complexed or bonded to the pre-light emitting molecule and the resulting light emitting molecule can be bonded to a surface or the pre-light emitting molecule can be first bonded to a surface and thereafter the luminescer can be complexed or otherwise bonded to the surface-bound pre-light emitting molecule. Alternatively, the luminescer can be complexed or otherwise bonded to a ligand or coordination site in a portion of the pre-light emitting molecule which is thereafter reacted with another portion of the pre-light emitting molecule already attached to the surface. Light emitting molecules can be treated to add substituent groups before or after they are bonded to a surface. Pre-light emitting molecules can be treated to add substituent groups before or after they are bonded to a surface.
Scheme E
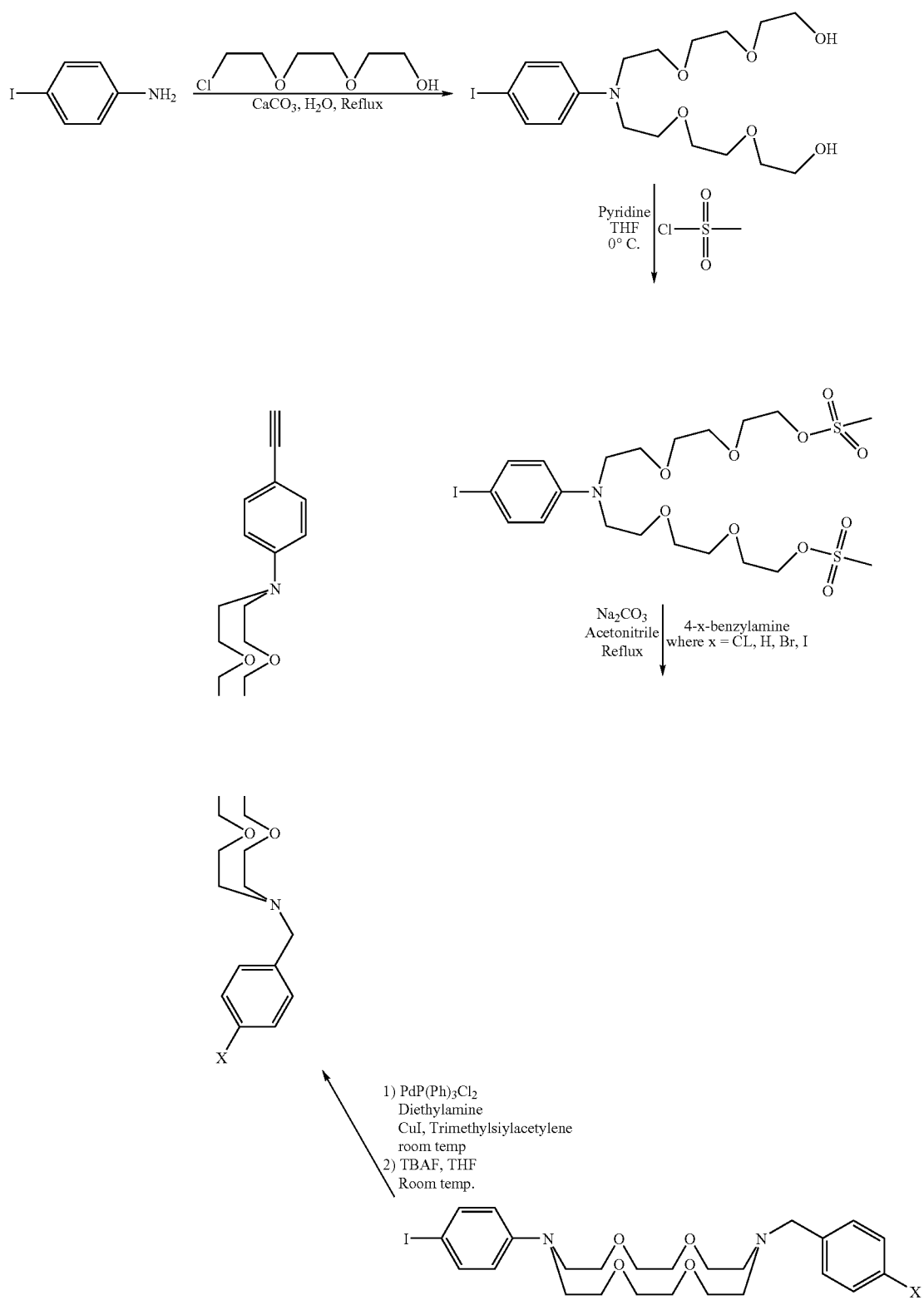

Schemes K and L illustrate various methods for synthesis of light emitting molecules of this invention. The methods illustrated show light-emitting molecules containing a macrocyclic ligand or multidentate ligand into which a luminescer metal atom can be introduced.

In Scheme K, the macrocyclic ligand is synthesized by addition of non-cyclic precursors of the macrocyclic ligand to at least a portion of a conjugated group. Thereafter the macrocyclic is formed by addition of both of the free ends of the two precursors to at least a portion of a charge transfer group.

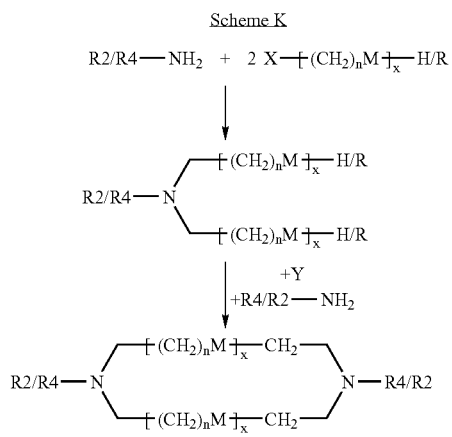

Scheme K where the variables are as defined above, Y is a leaving or protecting group and X is a halogen or reactive group.

Another example of reactions to form light emitting molecules include the following:

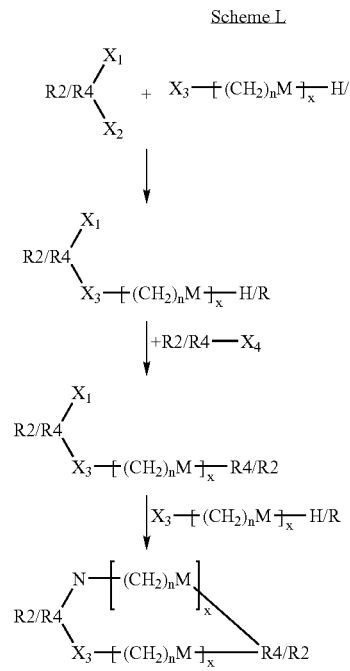

Scheme L where X1, X2, X3 and X4 are reactive groups or NH, O or S and the other variables are as defined above.

As known in the art and described herein, analogous reactions can be used to make other analogs.

Figure 4:
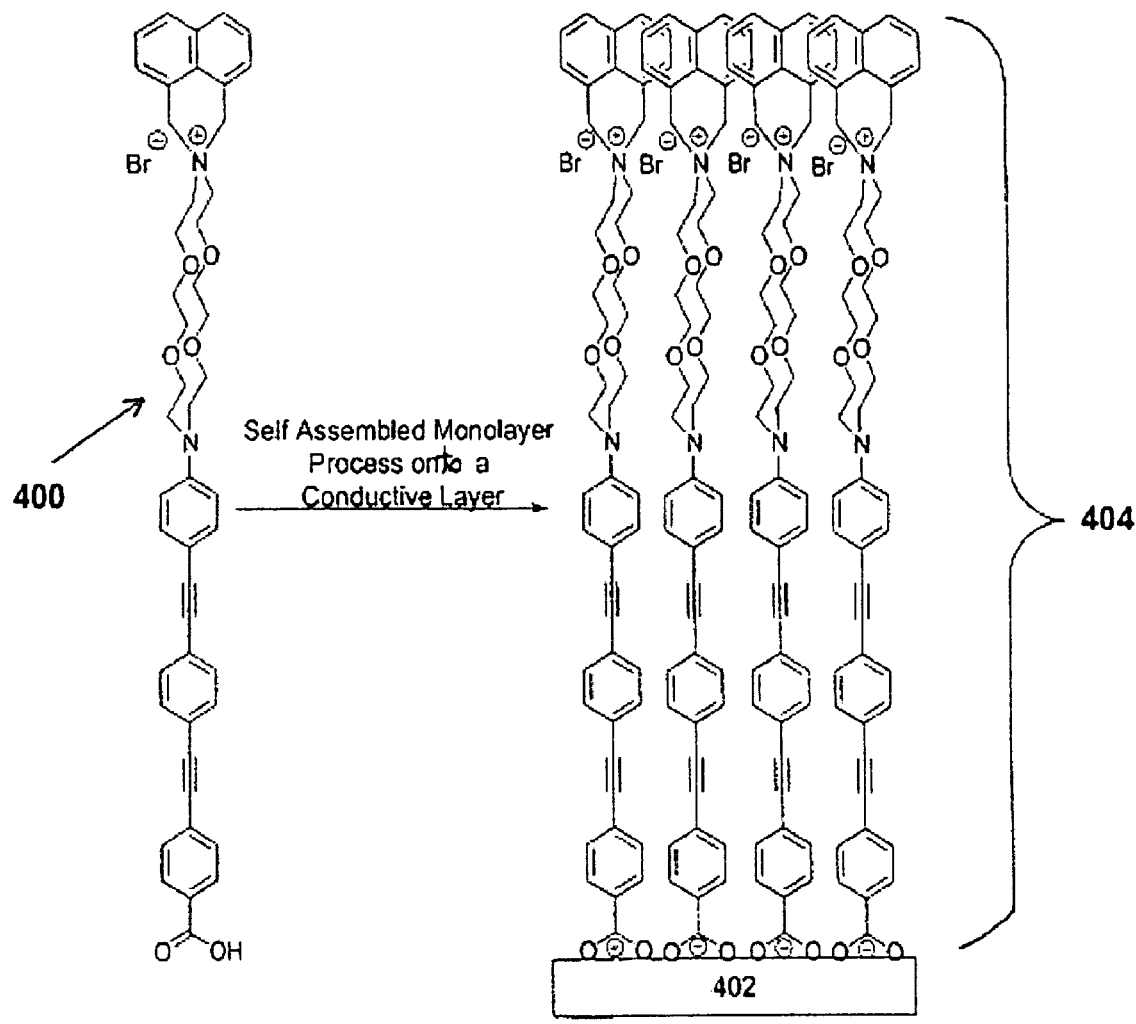
FIG. 4 and FIG. 5 illustrate a method of forming an organic light emitting device using a self-assembled monolayer process, according to an embodiment of the invention.

In the example illustrated in FIG. 4, a substrate is coated with a desired thickness of ITO. The ITO-coated substrate is dipped into a solution of light emitting molecules to form a self-assembled layer. The density of light emitting molecules on the surface of the substrate partly depends on the concentration of the solution, as known in the art. Also as known in the art, mixtures of solutions of light emitting molecules may be used. For example, light emitting molecules with different light emissive groups can be used to provide a surface with different light emitting characteristics (different wavelengths of emission or different intensity of emission, for example). Alternatively, a step-wise self-assembly process can be used, wherein a layer or partial layer of different light emitting molecules are deposited on the substrate. As known in the art, a dilute solution of light emitting molecules may be used to provide a surface with the desired level of coverage. In addition, a solution of molecular spacers can be used to provide the desired level of coverage. Molecular spacers can include molecules that are electrically insulating, such as nonconjugated aliphatic molecules with or without halogenated substitutions which can provide functions such as providing separation between regions on the substrate. Molecular spacers can also include electrically conductive molecules, such as conjugated hydrocarbon chains. Electrically conductive molecules can have different end groups, for attaching to other groups, or for synthesis purposes. Some examples of different end groups include halogens such as —F, —Br, or —I; —≡—; or —≡—Si—$(CH_3)_3$. Alternatively, the light emitting molecules can be formed step-wise on a substrate. One example of a first step of a step-wise formation of light emitting molecules is shown in Scheme F, where a substrate is etched in hydrogen peroxide, followed by a reaction with a bromophenyltrichlorosilane to form a layer on the substrate. Further steps in the step-wise process are shown in Schemes C and D, where a silane surface is further reacted to form a surface having a layer of light emitting molecules. The peroxide is used to form an oxide layer on the surface of the ITO, which allows the water to form a hydroxide on the surface so the bromophenyltrichlorosilane or trimethoxysilane can react to form the stable covalent O—Si bond.

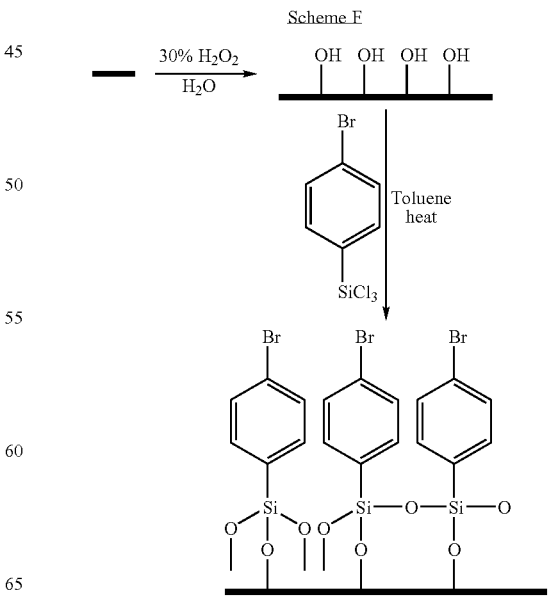

Scheme F

Schemes G, I and J show the formation of other pre-light emissive molecule of the invention, where parts of the surrounding structures such as the charge transport group are formed on the ends of the structure:
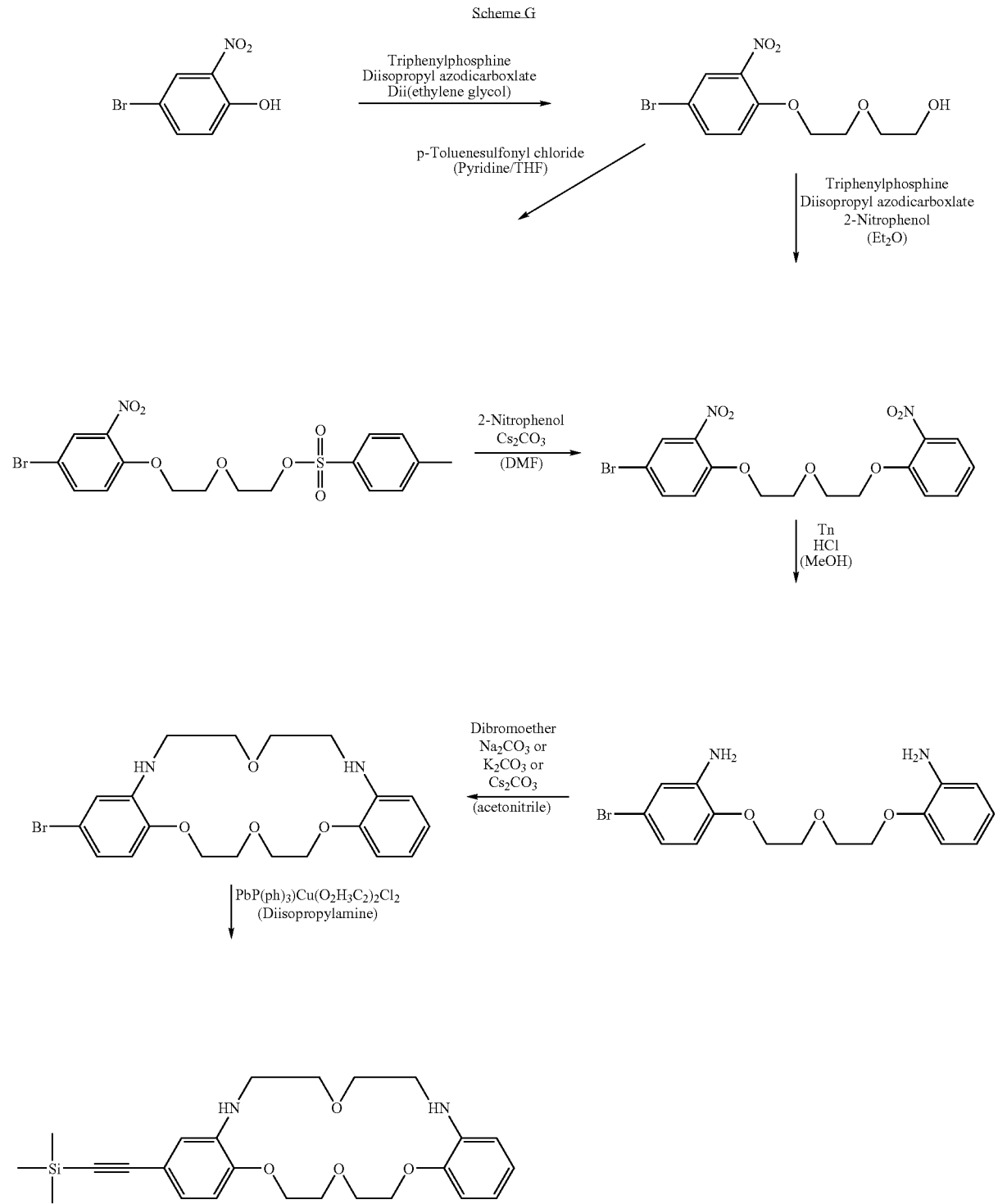

Scheme H shows portions of light emitting molecules of the invention that have been shown to emit red and green light:
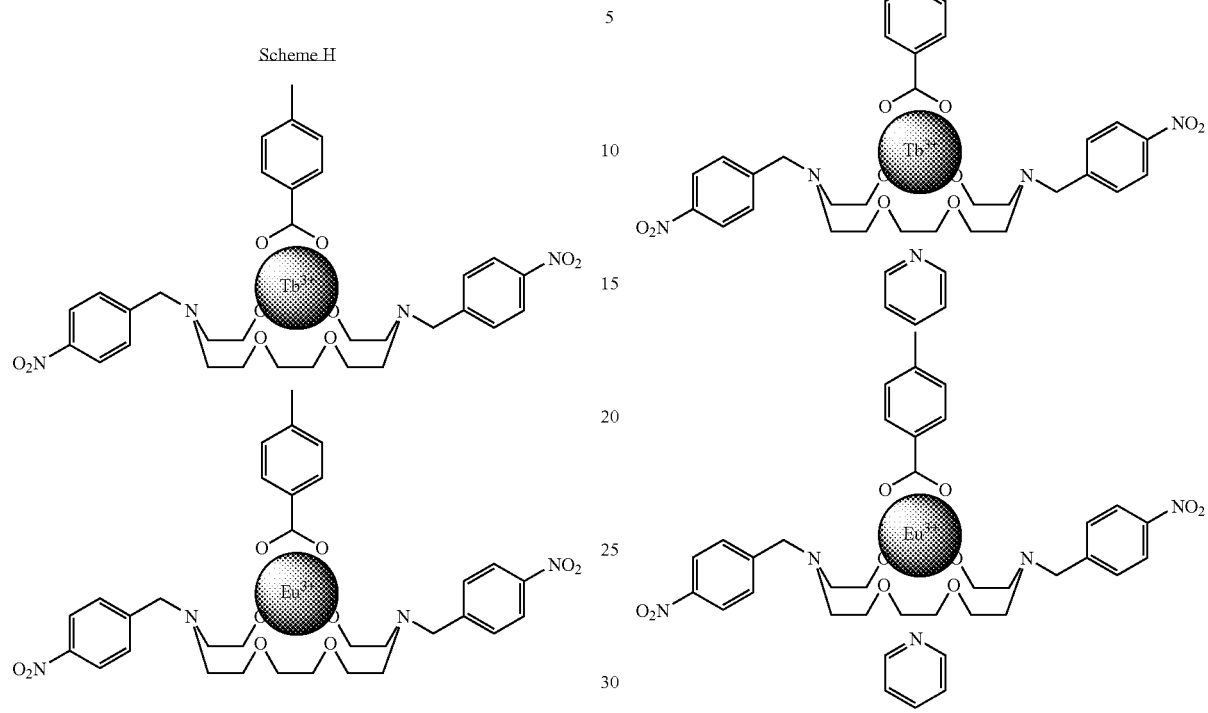
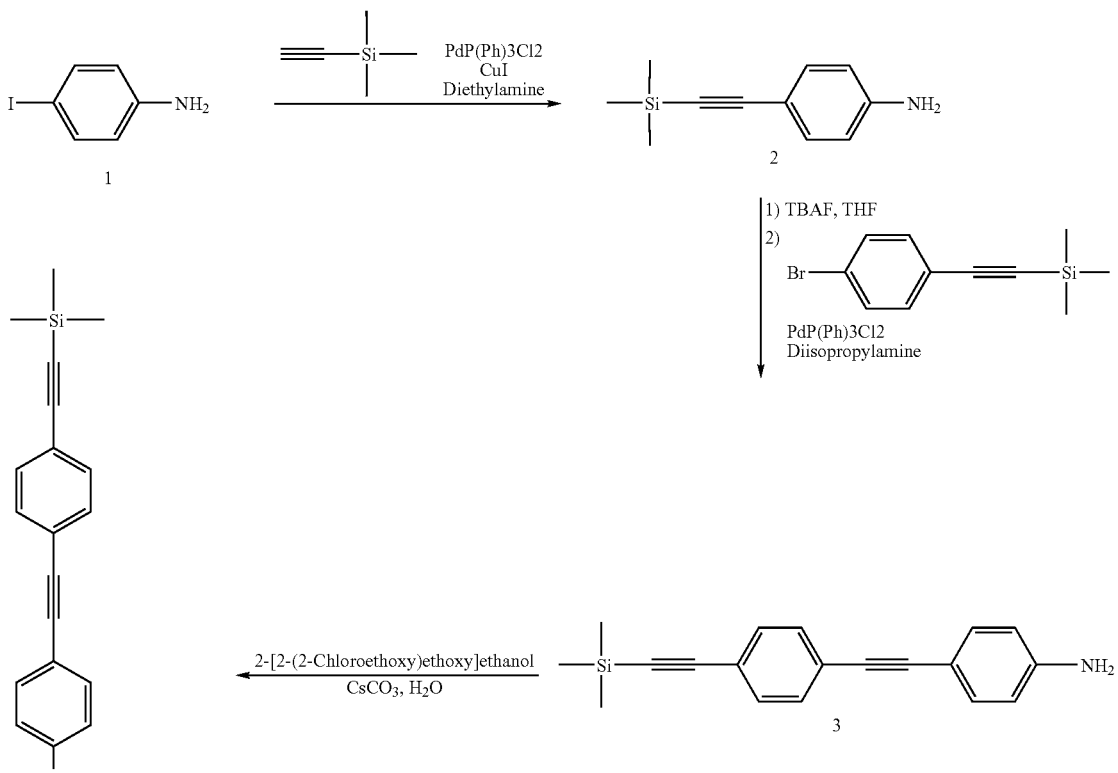

-continued
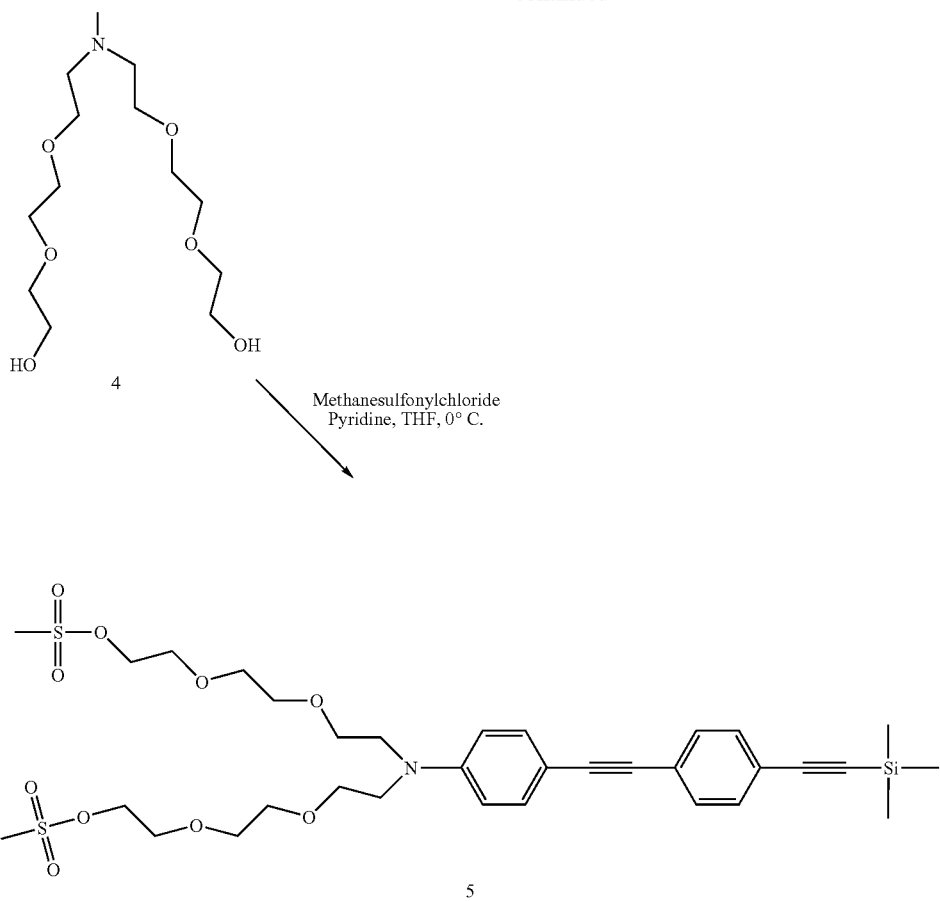
Scheme J
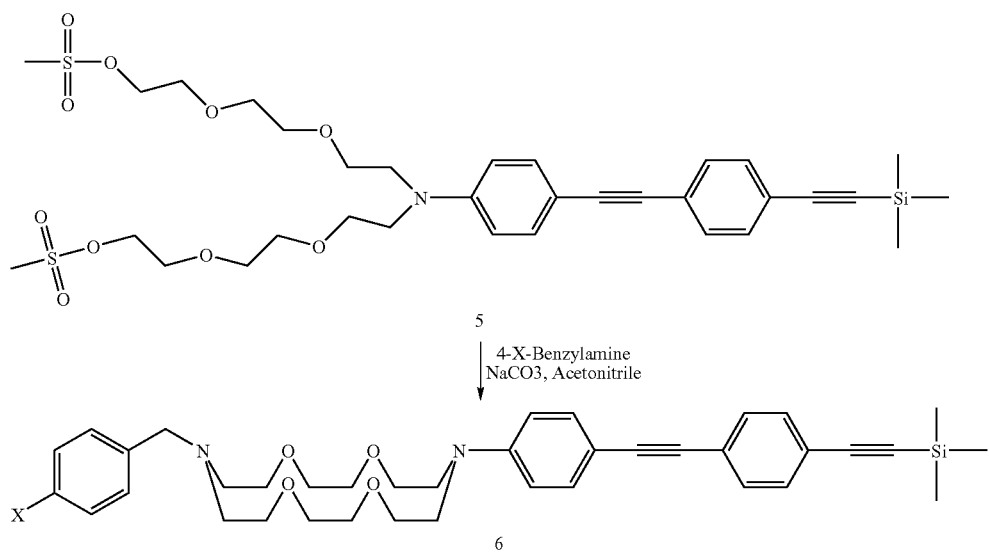
Where X is H, Cl, I, Br

Synthesis of precursors described in Schemes I and J follows:

Compound 1

To a flame dried round bottom flask was added 22.83 mmol 4-Iodoaniline, 0.41 mmol Pd catalyst, 1.25 mmol CuI and 50 ml diethylamine. The reaction mixture was purged 15 minutes with dry nitrogen, followed by the addition of 22.83 mmol trimethylsilyacetylene. The reaction mixture was allowed to stir over night at 30 degrees Celsius. Solvent removed via rotary evaporation. The residue taken up in DI water, extracted in ethylacetate, washed with brine and dried over sodium sulfate. Solvent removed via rotary evaporation and the material purified over a column of silica in 1:1 hexanes:ethylacetate. 3.74 g recovered for a yield of 86.5% from theoretical.

$H^1$ nmr ($CDCl_3$) δ; 7.26 (2 H, d), 6.56 (2 H, d), 4.10 (2 H, d), 0.23 (9 H, s).

Compound 2

To a round bottom flask was added compound 1, followed by 20 ml TBAF (Tetrabutylammoniumfluoride, 1.0 M in THF), and 6 ml THF. The mixture allowed to stirr overnight at room temperature. Solvent removed and residue run down a column of silica in 1:1 ethylacetate:hexanes.1.81 g recovered for a yield of 77% from theoretical $H^1$ nmr ($CDCl_3$) δ; 7.26 (2 H, d), 6.56 (2 H, d), 4.10 (2 H, d).

Compound 3

To a flame dried round bottom flask was added 15.36 mmol compound 2, 0.31 mmol Pd catalyst, 40 ml anhydrous dichloromethane and 60 ml diisopropylamine. The reaction mixture was purged with dry Nitrogen for 15 minutes and the temperature raised to 90 degrees Celsius and allowed to stir overnight. The reaction mixture allowed to cool to room temperature. Reaction mixture taken up in DI water, followed by extraction into ethylacetate, washings in brine and drying in sodium sulfate. Solvent removed by rotary evaporation and the residue purified over a column of silica in 1:1 ethylacetate:hexanes. 2.02 g recovered for a yield of 45% from theoretical.
$H^1$ nmr ($CDCl_3$) δ; 7.42 (4 H, s) 7.31 (2 H, d), 6.63 (2 H, d), 4.10 (2H, d) 0.26 (9 H, s).

Figure 10:
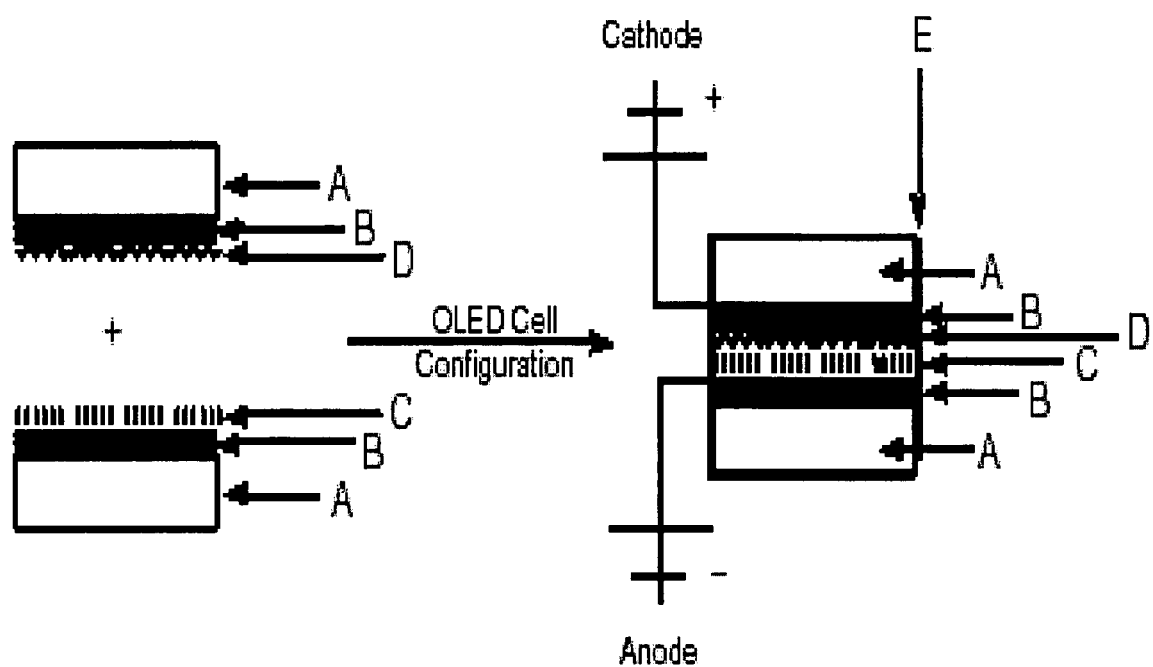
FIG. 10 illustrates one embodiment of a cell incorporating light emitting molecules.

In one use of the light emitting molecules of the invention, light emitting molecules are placed in a cell having two conductive surfaces surrounding the light emitting molecules, where an electrical current is passed through the cell, which causes the light emissive group to emit light. One example of a cell containing light emitting molecules is shown in FIG. 10. In FIG. 10, A designates the substrate, B designates a conductive film (for example ITO), C designates the light emitting molecules, D designates a conductive film (for example an electrically conductive polymer) and E designates dielectric glue used to hold the substrates together. Also shown in FIG. 10 is a current applied to the conductive films.

Methods of Forming Organic Light Emitting Devices

Figure 5:
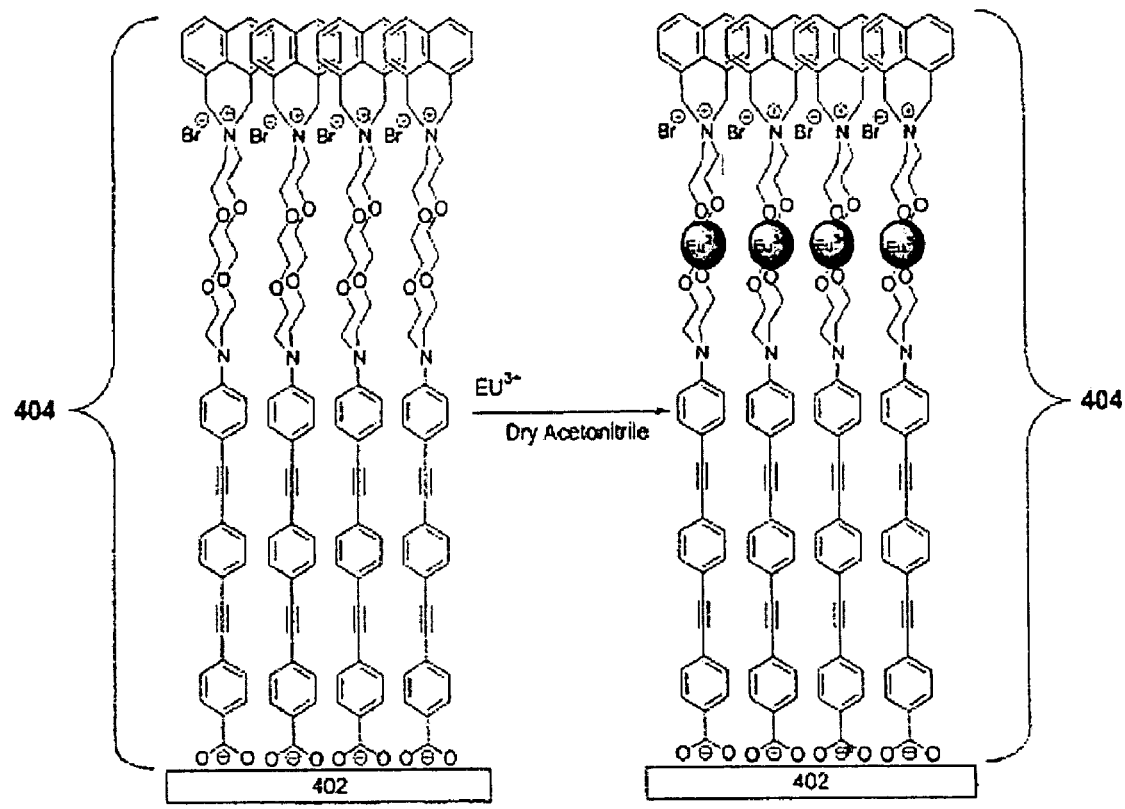

Organic light emitting devices in accordance with various embodiments of the invention can be formed using various methods. FIG. 4 and FIG. 5 illustrate a method of forming an organic light emitting device using a self-assembled monolayer process, according to an embodiment of the invention. Referring to FIG. 4, light emitting molecules (e.g., light emitting molecule 400) are initially formed without luminescers (i.e., are pre-emissive). Once formed, the light emitting molecules are then dispersed in a solvent to form a solution. As a result of the characteristics of anchoring groups of the light emitting molecules, the light emitting molecules can spontaneously align with respect to a common direction that is substantially orthogonal to a surface of the solution. The light emitting molecules are then transferred to a conductive layer 402 by contacting the conductive layer 402 with the solution. The light emitting molecules can bond to the conductive layer 402 to form a self-assembled monolayer 404 on the conductive layer 402. The description above can also be used to form silane groups on the surface followed by the solid state synthesis on the silane groups.

Referring to FIG. 5, luminescers are next added to the self-assembled monolayer 404. In particular, the self-assembled monolayer 404 is first treated by, for example, rinsing with dry acetonitrile and drying with a stream of dried nitrogen. Next, the self-assembled monolayer 404 is contacted with a solution of the luminescers. In particular, the self-assembled monolayer 404 is placed in a solution of $Eu^{3+}$ in dry acetonitrile to allow the $Eu^{3+}$ to bond to the light emitting molecules. Another conductive layer can then be formed or placed above the self-assembled monolayer 404 to form the organic light emitting device.

Formation of Light Emitting Molecules

As known in the art, various protecting and reacting groups can be used to synthesize the light emitting molecules and various components thereof described herein. The following describes one example of formation of a light emitting molecule of the invention.

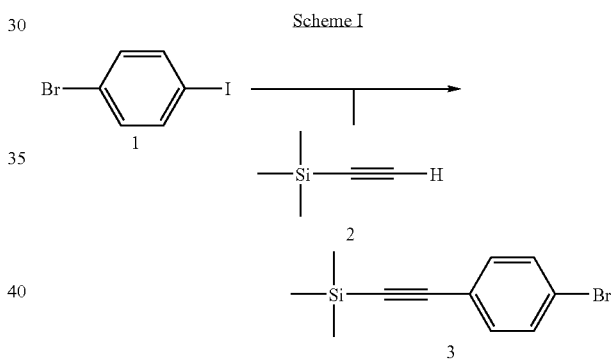

Scheme I 1-bromo-4-iodobenzene (1) can be reacted with trimethylsilylacetylene (2) to form 4-bromophenyl)ethynyl)trimethylsilane (3) as shown in Scheme I.

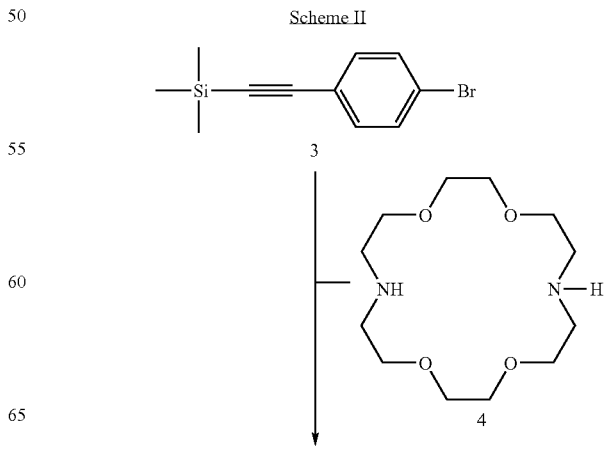

Scheme II

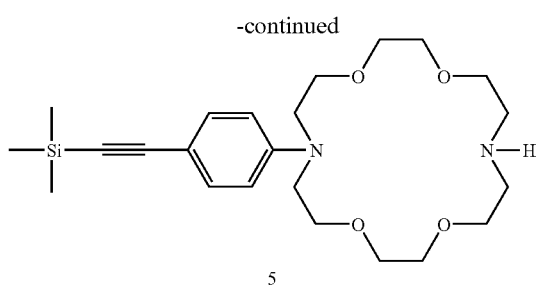

4-bromophenyl)ethynyl)trimethylsilane (3) can be reacted with 4,13-diaza-18-crown-6 (4) to form 4-(4-trimethylsilyl-ethynylphenyl)-4,13-diaza-18-crown-6 (5) as shown in Scheme II.

Scheme III 4-(4-trimethylsilylethynylphenyl)-4,13-diaza-18-crown-6 (5) can be reacted with 1-bromomethyl-4-cyanobenzene (6) to form 4-(4-trimethylsilylethynylphenyl)-13-((4-cyanophenyl)methyl)-4,13-diaza-18-crown-6 (7) as shown in Scheme III.

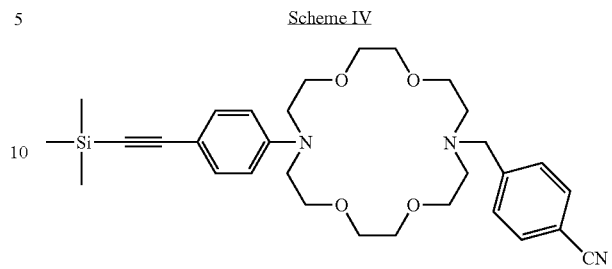

4-(4-trimethylsilylethynylphenyl)-13-((4-cyanophenyl)methyl)-4,13-diaza-18-crown-6 (7) can undergo a tms-deprotection reaction to form 4-(4-ethynylphenyl)-13-((4-cynophenyl)methyl)-4,13-diaza-18-crown-6 (8) as shown in Scheme IV.

Scheme V ((4-bromophenyl)ethynyl)trimethylsilane (3) can undergo a transhalogenation reaction to form ((4-iodophenyl)ethynyl)trimethylsilane (9) as shown in Scheme V.

Scheme VI

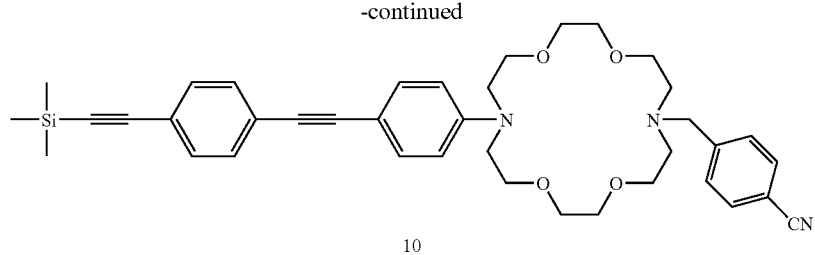
4-(4-ethynylphenyl)-13-((4-cyanophenyl)methyl)-4,13-diaza-18-crown-6 (8) can be reacted with ((4-iodophenyl)ethynyl)trimethylsilane (9) to form 4-(4-(4-trimethylsilylethynylphenyl)-13-((4-cyanophenyl)methyl)-4,13-diaza-18-crown-6 (10) in an electrophilic substitution reaction as shown in Scheme VI.
Scheme VII
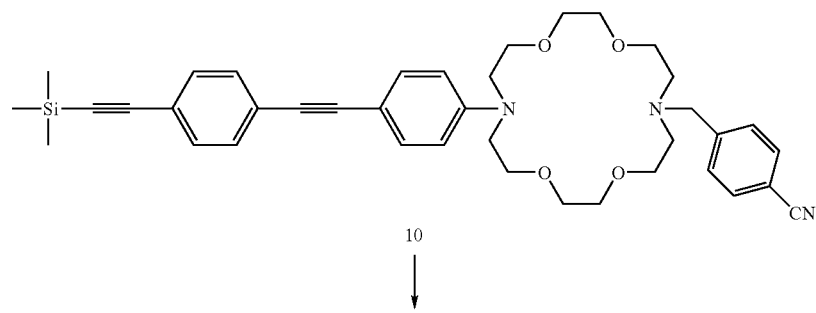
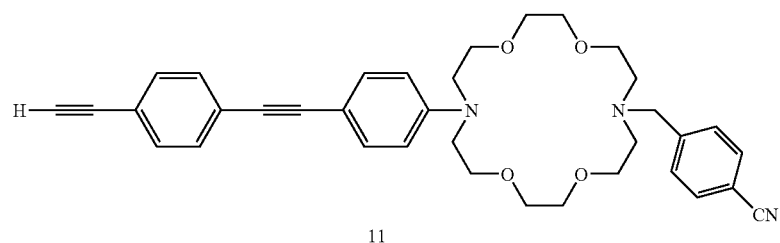

4-(4-(4-trimethylsilylethynylphenyl)ethynylphenyl)-13-((4-cyanophenyl)methyl)-4,13-diaza-18-crown-6 (10) can undergo a tms-deprotection reaction to form 4-(4-(4-ethynylphenyl)ethynylphenyl)-13-((4-cyanophenyl)methyl)-4,13-diaza-18-crown-6 (11) as shown in Scheme VII.

Scheme VIII

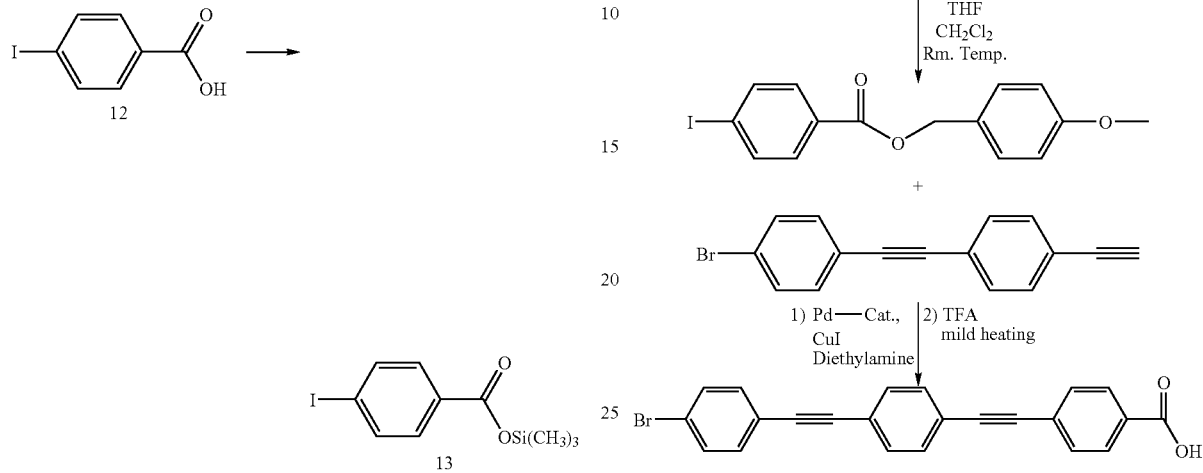

Scheme VIIIA

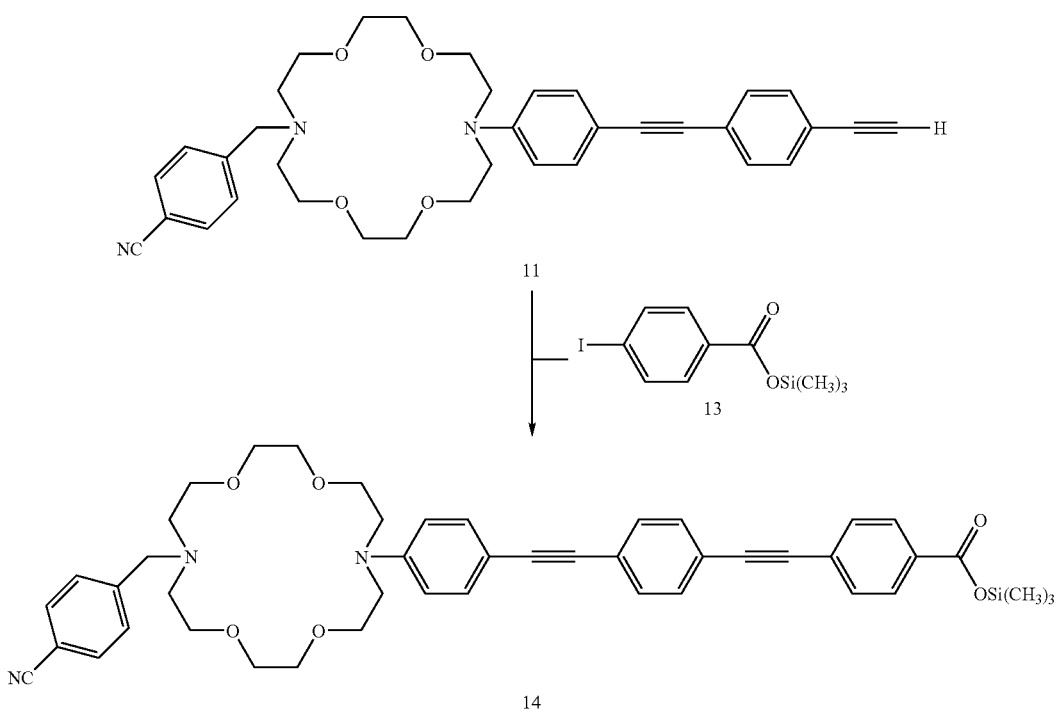

Scheme IX 4-iodobenzoic acid (12) can undergo an acid protection via esterification reaction to form 1-iodo-4-trimethylsiloxycarbonyl-benzene 13 as shown in Scheme VIII.

Alternatively, the PMB protecting group can be used, as shown in Scheme VIIIA.

4-(4-(4-ethynylphenyl)ethynylphenyl)-13-((4-cyanophenyl)methyl)-4,13-diaza-18-crown-6(11) and 1-iodo-4-trimethylsiloxycarbonyl-benzene (13) can be reacted in an electrophilic substitution reaction to form 4-(4-(4-(4-trimethylsiloxycarbonylphenyl)ethynylphenyl)ethynylphenyl)

ethynylphenyl) -13-((4-cyanophenyl)methyl) -4,13-diaza-18-crown-6 (14) as shown in Scheme IX.

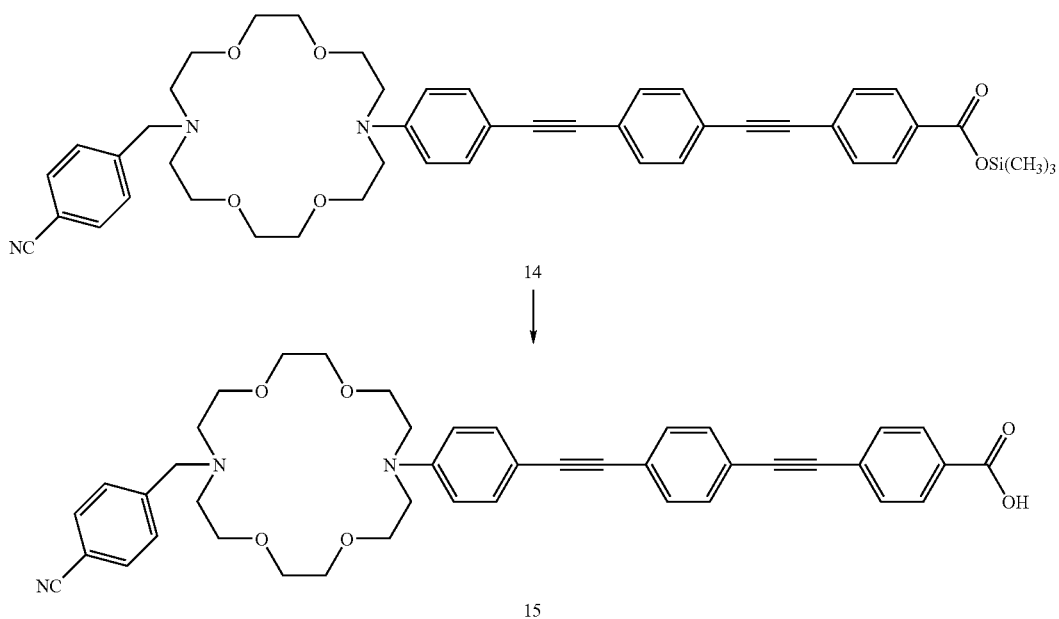

Scheme X 4-(4-(4-(4-trimethylsiloxycarbonylphenyl)ethynylphenyl)ethynylphenyl)-13-((4-cyanophenyl)methyl)-4,13-diaza-18-crown-6 (14) can undergo an acid deprotection eaction to form 4-(4-(4-(4-carboxyphenyl)ethynylphenyl)ethynylphenyl)-13-((4-cyanophenyl)methyl)-4,13-diaza-18-crown-6 (15) as shown in Scheme X.

Formation of Organic Light Emitting Device

Figure 6:
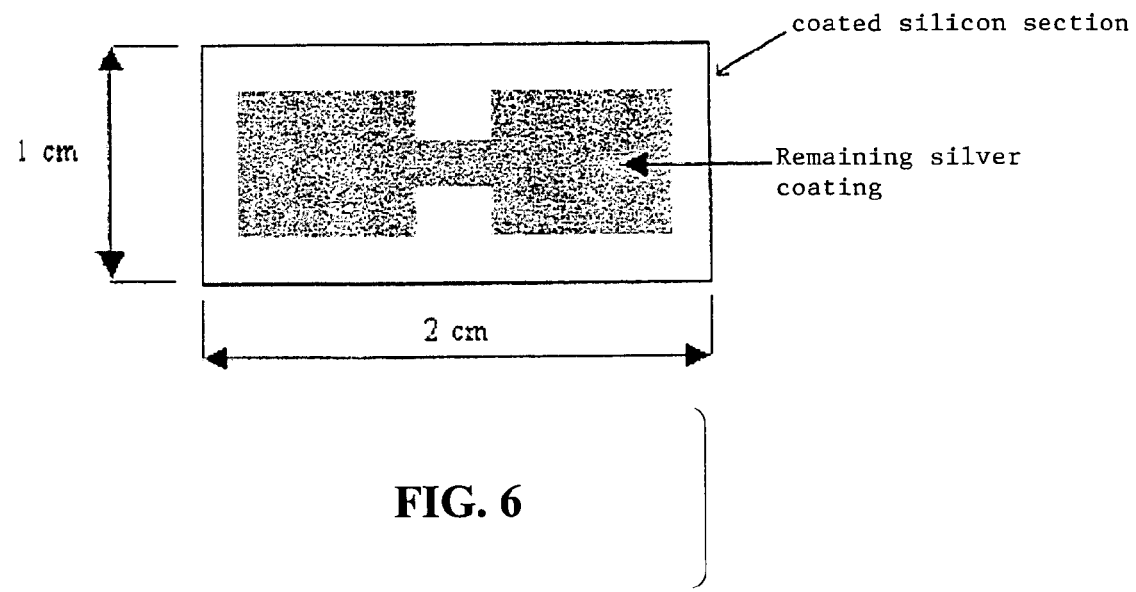
FIG. 6, FIG. 7, and FIG. 8 illustrate an example of forming an organic light emitting device using a self-assembled monolayer process, according to an embodiment of the invention.
Figure 7:
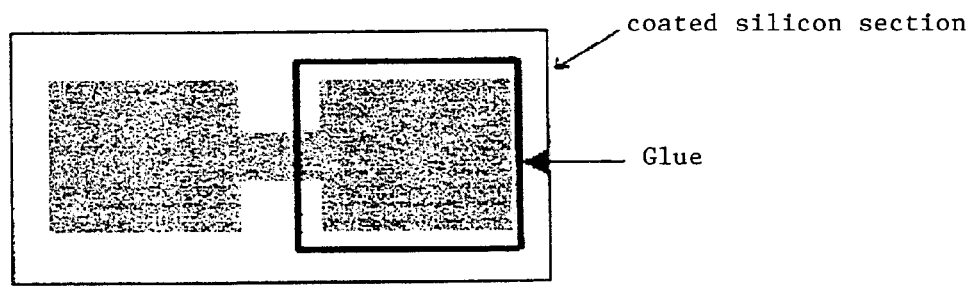
Figure 8:
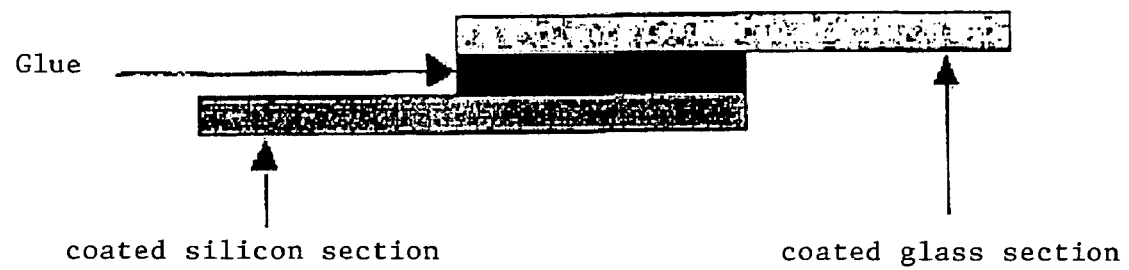

FIG. 6, FIG. 7, and FIG. 8 illustrate an example of forming an organic light emitting device using a self-assembled monolayer process. A 4-inch, highly-doped silicon wafer is coated by vapor deposition. In particular, the silicon wafer is initially coated with chromium to a thickness in the range of 8 nm to 12 nm and is then coated with silver (99.99%) to a thickness in the range of 70 nm to 110 nm. The coated silicon wafer is then diced to form a 1 cm×2 cm coated silicon section, which is washed with dry ethanol and dried with a stream of dry nitrogen. The coated silicon section is then patterned by $O_2$-plasma etching in conjunction with a shadow mask as illustrated in FIG. 6. Once patterned, the coated silicon section is further cleaned in an ethanol/ultrasonic bath and dried with a stream of dry nitrogen.

The coated silicon section is immersed in a solution of pre-light emitting molecules (15, $2.5\times10^{-4}$ mol in dry THF, toluene, and acetonitrile (1:1:1)) under an atmosphere of dry nitrogen for 16 hours at 22° C. The light emitting molecules bond to the coated silicon section to form a self-assembled monolayer on the coated silicon section. The coated silicon section with the self-assembled monolayer is washed with dry ethanol and dried with a stream of dry nitrogen.

The coated silicon section with the self-assembled monolayer is placed in a nitrogen purged vessel and is partially immersed (1 cm depth) in a solution of europium acetate in dry acetonitrile at a temperature in the range of about 50° C. to about 55° C. The solution is maintained at that temperature for about 30 minutes to about 2 hours with gentle stirring. The solution is then removed under an inert atmosphere, and the coated silicon section with the self-assembled monolayer is rinsed with dry acetonitrile and dried with a stream of dry nitrogen.

A 8-inch glass substrate with a layer of indium tin oxide is spin-coated with an electrically conductive polymeric material on the indium tin oxide side. Next, the coated glass substrate is dried with a stream of dry nitrogen. The coated glass substrate is then diced to form a 1 cm×2 cm coated glass section, which is washed with dry ethanol and dried with a stream of dry nitrogen.

A thin line of UV or heat curable epoxy (preferably with few or no fillers) is deposited on the coated silicon section on the self-assembled monolayer side as illustrated in FIG. 7. As illustrated in FIG. 8, the coated glass section is positioned over the coated silicon section to form a laminate, such that the laminate provides two electrical contact points. Once the coated glass section is thus positioned, pressure is applied evenly, and the glue is cured. The electrically conductive polymeric material is bonded to the self-assembled monolayer.

Each of the patent applications, patents, publications, and other published documents mentioned or referred to in this specification is herein incorporated by reference in its entirety, to the same extent as if each individual patent application, patent, publication, and other published document was specifically and individually indicated to be incorporated by reference. References cited herein are incorporated by reference herein to provide among other things additional description of synthesis of light emitting molecules and portions thereof, particularly any macrocyclic ligands therein, of choice of light emissive group or luminescer for a given application, and of construction and application of optical devices employing OLEDs.

While the invention has been described with reference to the specific embodiments thereof, it should be understood by those skilled in the art that various changes may be made and equivalents may be substituted without departing from the true spirit and scope of the invention as defined by the appended claims. In addition, many modifications may be made to adapt a particular situation, material, composition of matter, method, process step or steps, to the objective, spirit and scope of the invention. All such modifications are intended to be within the scope of the claims appended hereto. In particular, while the methods disclosed herein have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations are not limitations of the invention. In instances herein where a numerical range is recited, all individual members of the range recited used all sub-ranges of the range recited are intended to be encompassed by the range recited.

References relating to molecular wire synthesis include R. P. Hsung et al., Organometallics 1195, 14, 4808.

References relating to analog cryptand of scheme G include: B. Gersch et al., Tetrahedron Letters 1996, 37, 13, 2213.

References relating to PMB protecting group include S. Torii et al., Org. Chem 1991, 56, 3633.

P. M. Borsenberger et al., Phys. Stat. Sol. (a) 140, 9 (1993) (Eastman Kodak) is a review article on charge transport materials in molecularly doped polymers.

References on making cryptands and analogs include:
G. Das et al., Tetrahedron 56 (2000) 1501
V. P. Munk et al., Aust. J. Chem. 2002, 55, 523
K. R. Fewings et al., Aust. J. Chem. 1999, 52, 1109
J. C. Aguilar et al., Talanta 54 (2001) 1195
C. D. Hall et al., J. Organometallic Chem. 547 (1997) 281
L. Schreyeck et al., Microporous and Mesoporous Materials 22 (1998) 87

The following list of references describes organic light emitting displays, synthesis methods and other aspects of organic light emitting devices.
L. A. Bumm et al., Science 271:1705, 1996.
C. P. Collieretal., Science 285:391, 1999.
W. B. Davis et al., Nature 396:960, 1998.
Y. Shirota, J. Mater. Chem. 10:1, 2000.
M. R. Robinson et al., Advanced Materials 12(22):1701, 2000.
S. Capecchi et al., Advanced Materials 12(21):1591, 2000.
E. Tutis et al., J. Appl. Phys. 89(1):430, 2000.
A. R. Melnyk, Is & T's 8$^{th}$ Inter. Congress, Advances in Non-impact Printing Technologies, Williamsberg, Va., 1992.
K. Y. Law, Chem. Rev. 93:449, 1993.
P. Sigand et al., J. Appl. Phys. 89:466, 2001.
S. T. Lee et al., Appl. Phys. Lett. 75:1404, 1999.
A. R. Schlatman et al., Appl. Phys. Lett. 69:1764, 1996.
P. Sigaud et al., J. Appl. Phys. 89(1):466, 2000.
J. He et al., J. Appl. Phys. 88(5):2386, 2000.
M. Carrard et al., Thin Solid Films 352:189, 1999.
A. Kumar et al., Appl. Phys. Lett. 63:2002, 1993.
Y. Xia et al., Science 273:347, 1996.
X. Y. Hou et al., Advanced Materials 112(4):265, 2000.
V. Cimrova et al., Synth. Mat. 76:125, 1996.
N. Tessler, Appl. Phys. Lett. 77:12, 2000.
H. Becker et al., Phys. Rev. B 56:1893, 1997.
D. J. Pinner et al., J. Appl. Phys. 86:5116, 1999.
P. W. M. Blom et al., Polym. Adv. Technol. 9:390, 1998.
J. C. Scott etal., Chem. Phys. Lett. 299:115, 1999.
U. Wolf et al., Appl. Phys. Lett. 74:3848, 1999.
A. J. Cambell et al., J. Appl. Phys. 84:6737, 1998.
T. Mari et al., Jpn. J. Appl. Phys. Part 2, 345:L845, 1995.
M. Fajikira et al., Appl. Phys. Lett. 68:1787, 1996.
E. M. Han et al., Chem. Lett. 1:57, 1995.
A. A. Dhirani et al., J. Am. Chem. Soc. 118:3319, 1996.
R. G. Nuzzo et al., J. Am. Chem. Soc. 105:4481, 1983.
R. G. Nuzzo et al., J. Am. Chem. Soc. 109:2358, 1987.
M. D. Porter et al., J. Am. Chem. Soc. 109:3559, 1987.
E. B. Troughton et al., Langmuir 4:365, 1988.
C. D. Bain et al., J. Am. Chem. Soc. 111:321, 1989.
R. G. Nuzzo et al., J. Am. Chem. Soc. 112:558, 1990.
G. Hathner et al., Langmuir 9:1955, 1993.
I. Willner et al., J. Am. Chem. Soc. 116:9365, 1994.
J. Spinke et al., J. Chem. Phys. 99:7012, 1993.
M. Weisser et al., Sens. Actuators B 39/39:58, 1997.
T. J. Gardner et al., J. Am. Chem. Soc. 117:6927, 1995.
A. Ulman, Ulthrathin Organic Films, Academic Press, San Diego, 1991.
L. H. Dubois et al., Ann. Rev. Phys. Chem. 43:437, 1992.
J. Xu et al., Colloid Interface Sci. 175:138, 1995.
A. Ulman, Chem. Rev. 96:1533, 1996.
G. E. Poirier, Chem. Rev. 97:1117, 1997.
C. D. Bain et al., J. Am. Chem. Soc. 111:7155, 1989.
G. Nelles et al., Langmuir 14:808, 1998.
C. D. Bain et al., J. Am. Chem. Soc. 111:321, 1998.
E. Wurtzberg et al., J. Chem. Phys. 62:208, 1975.
V. Balzani et al., Angew. Chem. Int. Ed. Engl. 28:1266, 1987.
S. P. Sinha, in S. P. (ed.), Systems and Properties of the Lanthenides, NATO ASI Series 109, Reidel, Dordrecht, 451, 1963.
Y. Hans et al., J. Phys. Chem. 75:3677, 1971.
W. W. Horrocks et al., Accounts Chem. Res. 14:384, 1981.
V. Balzani et al., Supramolecular Photochemistry, Ellis Horwood, West Sussex, UK, 1991.
G. A. Crosby et al., J. Chem. Phys. 34:743, 1961.
M. I. Bhaumik et al., J. Phys. Chem. 69:275, 1965.
J. A. Yu et al., Chem. Phys. Lett. 187(n3):263, 1991.
B. Alpha et al., Photochem. Photobiol. 52:229, 1990.
G. Blasse et al., Chem. Phys. Lett. 146:347, 1988.
G. Blasse et al., J. Phys. Chem. 92:2419, 1988.
L. H. Dubois et al., Ann. Rev. Phys. Chem. 43:437, 1992.
J. M. Lehn, Angew. Chem. Int. Ed. Engl. 27:89, 1988.
J. M. Lehn, J. Incl. Phneom. 6:351, 1988.
J. M. Lehn, Supramolecular Chemistry, VCH, Weimhein, Germany, 1995.
M. A. Mortellaro et al., Chemtech. 17, 1996.
Y. T. Tao, J. Am. Chem. Soc. 115:4350, 1993.
M. G. Samant et al., Langmuir 9:1082, 1993.
A. H. M. Sondag et al., Langmuir 8:1127, 1992.
D. E. King, J. Vac. Sci. Technol. A. 13:3, 1995.

I claim:
1. A light emitting molecule having the formula:

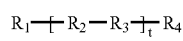

(I)

wherein t is an integer from 1 to 19; R1 is an anchoring group, said anchoring group including at least one atom selected from the group consisting of: a nitrogen atom, an oxygen atom, a silicon atom and a sulfur atom; R2 is a conjugated group; R3 is a light emissive group; and R4 is a charge transfer group, wherein R3 has the formula:

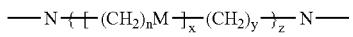

where M is independently selected from the group consisting of: O, NH, NR and S, where R is a small alkyl group; n and y are independently integers from 1 to 19; x is an integer from 1 to 19; and z is an integer from 1 to 3.

2. The molecule of claim 1, wherein R3 has the formula:

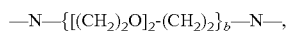

wherein b is 2 or 3.

3. A light emitting molecule having the formula:

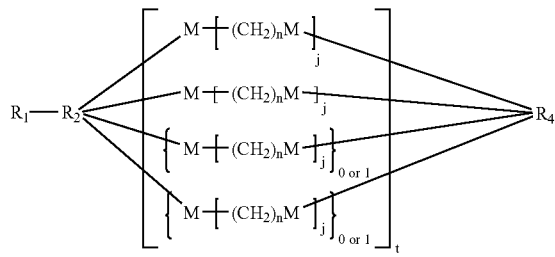

wherein R1 is an anchoring group, said anchoring group including at least one atom selected from the group consisting of: a nitrogen atom, an oxygen atom, a silicon atom and a sulfur atom; R2 is a conjugated group; R4 is a charge transfer group; M is independently selected from the group consisting of: O, NH, NR and S where R is a small alkyl group; n is an integer from 1 to 3; j is an integer from 2 to 5; and t is an integer from 1 to 19.

4. The molecule of claim 3, wherein R2 comprises one or more groups selected from the group consisting of: alkenylene, alkynylene, imidylene, and arylene.

5. The molecule of claim 4, wherein R2 has the formula:

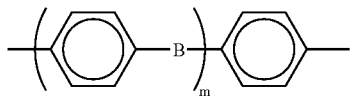

where m is an integer from 1 to 19 and B is an alkenylene, alkynylene or imidylene group.

6. The molecule of claim 5, wherein m is 1 to 6.

7. The molecule of claim 3, wherein R4 is one or more groups selected from the group consisting of: hydrogen, alkyl groups, alkylene groups, alkenyl groups, alkenylene groups, alkynyl groups, alkynylene groups, aryl groups, arylene groups, iminyl groups, iminylene groups, hydride groups, halo groups, hydroxy groups, alkoxy groups, carboxy groups, thio groups, alkylthio groups, disulfide groups, cyano groups, nitro groups, amino groups, alkylamino groups, dialkylamino groups, silyl groups, and siloxy groups.

8. The molecule of claim 3, wherein the molecule has one or more metal atoms coordinated thereto.

9. The molecule of claim 8, wherein a metal atom coordinated to the molecule is a lanthanide metal ion.

10. The molecule of claim 9, wherein said lanthanide metal ion is one or more of $Eu^{3+}$, $Dy^{3+}$, and $Tb^{3+}$.

11. A light emitting device comprising:
two opposing substrates, each substrate having a conductive layer, said conductive layers positioned on the inner surfaces of the substrates,
one or more light emitting molecules positioned between the two opposing substrates, said light emitting molecules having the formula:

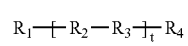

(I)

wherein t is an integer from 1 to 4; R1 is an anchoring group, said anchoring group including at least one atom selected from the group consisting of: a nitrogen atom, an oxygen atom, a silicon atom and a sulfur atom; R2 is a charge transfer group.

12. The device of claim 11, wherein the light emissive group has one or more metal atoms coordinated thereto.

13. The device of claim 12, wherein a metal atom coordinated to the light emissive group is a lanthanide metal ion.

14. The device of claim 13, wherein said lanthanide metal ion is one or more of $Eu^{3+}$, $Dy^{3+}$, and $Tb^{3+}$.

15. The device of claim 13, wherein the anchoring group is covalently bound to one of the opposing substrates.

16. A pixel element, comprising:
one or more light emitting molecules, each light emitting molecule comprising:
an anchoring group,
a conjugated group bonded to said anchoring group;
a light emissive group bonded to said conjugated group.

17. The pixel element of claim 16, wherein said anchoring group is configured to bond said light emitting molecule to a first conductive layer.

18. The pixel element of claim 16, wherein said light emissive group includes a luminescer.

19. The pixel element of claim 18, wherein said luminescer is a lanthanide metal ion.

20. The pixel element of claim 16, wherein said light emitting molecule further comprises a charge transfer group bonded to said light emissive group and configured to bond said light emitting molecule to a second conductive layer.

21. An organic light emitting device, comprising:
a plurality of pixel elements arranged in an array, at least one pixel element of said plurality of pixel elements comprising a light emitting molecule that comprises
an anchoring group covalently bound to a first conductive layer,
a charge transport group bonded to said anchoring group,
a light emissive group bonded to said charge transport group, and
a charge transfer group bonded to said light emissive group and bonded to a second conductive layer.

22. The organic light emitting device of claim 21, wherein said plurality of pixel elements are substantially aligned with respect to a common direction.

23. The organic light emitting device of claim 21, wherein said charge transport group comprises at least one of an alkenylene group, an alkynylene group, an arylene group, and an iminylene group.

24. The organic light emitting device of claim 21, wherein said charge transport group comprises a conjugated group having a formula:

wherein m is an integer in the range of 1 to 19, A is an arylene group, and B is one of an alkenylene group, an alkynylene group, and an iminylene group.

25. The organic light emitting device of claim 21, wherein said light emissive group comprises a lanthanide metal ion.

26. A display device, comprising:
a first conductive layer;
a second conductive layer; and
a plurality of light emitting molecules positioned between said first conductive layer and said second conductive layer, at least one light emitting molecule of said plurality of light emitting molecules comprising
an anchoring group bonded to said first conductive layer,
a conjugated group bonded to said anchoring group,
a light emissive group bonded to said conjugated group.

27. The display device of claim 26, wherein said plurality of light emitting molecules is substantially aligned with respect to a common direction, said common direction defines an angle with respect to a direction orthogonal to said first conductive layer, said angle being in the range of 0 to 25 degrees.

28. The display device of claim 26, wherein each light emitting molecule of said plurality of light emitting molecules extends between said first conductive layer and said second conductive layer.

29. The display device of claim 26, wherein said anchoring group comprises an atom configured to form a chemical bond with said first conductive layer, said atom being one of a nitrogen atom, an oxygen atom, a silicon atom, and a sulfur atom.

30. The display device of claim 26, wherein said conjugated group comprises a plurality of conjugated $\pi$-bonds.

31. The display device of claim 26, wherein said conjugated group comprises at least one arylene group.

32. The display device of claim 26, wherein said conjugated group further comprises at least one alkenylene group bonded to two successive arylene.

33. The display device of claim 26, wherein said conjugated group further comprises at least one alkynylene group bonded to two successive arylene.

34. The display device of claim 26, wherein said conjugated group further comprises at least one iminylene group bonded to two successive arylene groups.

35. The display device of claim 26, wherein said light emissive group is configured to emit light having a wavelength in the range of 410 nm to 650 nm.

36. The display device of claim 26, wherein said light emissive group comprises a metal ion.

37. The display device of claim 36, wherein said metal ion is a lanthanide metal ion.

38. The display device of claim 37, wherein said lanthanide metal ion is one of $Eu^{3+}$, $Dy^{3+}$, and $Tb^{3+}$.

39. The display device of claim 26, wherein said at least one molecule further comprises a charge transfer group bonded to said light emissive group and to said second conductive layer.

* * * * *